(12) United States Patent
Yao et al.

(10) Patent No.: US 11,440,931 B2
(45) Date of Patent: *Sep. 13, 2022

(54) CROCINS COMPOUNDS AND USES THEREOF

(71) Applicant: Jinan University, Guangdong (CN)

(72) Inventors: Xinsheng Yao, Guangdong (CN); Yang Yu, Guangdong (CN); Dan Zhang, Beijing (CN); Yang Ni, Guangdong (CN); Xiuqi Bao, Beijing (CN); Lin Li, Guangdong (CN); Caixia Zang, Beijing (CN); Hao Gao, Guangdong (CN); Yuanpeng Zheng, Beijing (CN)

(73) Assignee: Jinan University, Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/097,166

(22) PCT Filed: Mar. 16, 2017

(86) PCT No.: PCT/CN2017/076911
§ 371 (c)(1),
(2) Date: Oct. 26, 2018

(87) PCT Pub. No.: WO2017/185900
PCT Pub. Date: Nov. 2, 2017

(65) Prior Publication Data
US 2019/0177354 A1  Jun. 13, 2019

(30) Foreign Application Priority Data

Apr. 29, 2016 (CN) .......................... 201610284974.6

(51) Int. Cl.
*C07H 13/06* (2006.01)
*C07H 1/08* (2006.01)
*C07H 13/04* (2006.01)
*A61K 31/7024* (2006.01)

(52) U.S. Cl.
CPC ......... *C07H 13/06* (2013.01); *A61K 31/7024* (2013.01); *C07H 1/08* (2013.01); *C07H 13/04* (2013.01)

(58) Field of Classification Search
CPC .......... C07H 1/08; C07H 13/04; C07H 13/06; A61K 31/7024
USPC .......................................................... 514/25
See application file for complete search history.

(56) References Cited

U.S. PATENT DOCUMENTS

2010/0210572 A1  8/2010  Eidenberger

FOREIGN PATENT DOCUMENTS

| CN | 1123663 A | 6/1996 | | |
|---|---|---|---|---|
| CN | 102516325 A | 6/2012 | | |
| CN | 102802636 A | 11/2012 | | |
| CN | 103601764 A | 2/2014 | | |
| CN | 103665059 A | * 3/2014 | ............ | C07H 13/06 |
| CN | 103665060 A | 3/2014 | | |

OTHER PUBLICATIONS

Papandreou et al, J. Agri. Food Chem., 2006, 54, 8762-8769.*
Poma et al, Anti-Inflammatory and Anti-Allergy Agents in Medicinal Chemistry 2012, 11, 37-51.*
Lee et al, Bioorganic and Medicinal Chemistry Letters, 2013, 23, 2140-2144.*
The Merck Manual, 16th Edn. 1992, pp. 1488-1489, 1493-1494.*
The Merck Manual, 1992, 16th Edn., p. 1403.*
Yoshino et al., Pharmacology & Pharmacy, 2014, 5, 37-42.*
International Search Report received in PCT/CN2017/076911 dated Jun. 20, 2017.
Written Opinion received in PCT/CN2017/076911 dated Jun. 20, 2017.
First Office Action received in CN201610284974 dated Nov. 28, 2016.
Second Office Action received in CN201610284974 dated Mar. 21, 2017.
Third Office Action received in CN201610284974 dated Jul. 3, 2017.
Papandreou, et al., "Inhibitory activity on amyloid-beta aggregation and antioxidant properties of Crocus sativus stigmas extract and its crocin constituents", Nov. 15, 2006, pp. 8762-8768, vol. 54, No. 23, Publisher: J Agric Food Chem.
Tarantilis, et al., "Determination of saffron (*Crocus sativus* L.) components in crude plant extract using high-performance liquid chromatography-UV-visible photodiode . . . ", May 5, 1995, pp. 107-118, vol. 699, No. 1-2, Publisher: J Chromatogr A.
Yu, Yang, "studies on chemical constituents of Gardenia Jasminoides for the Treatment of Alzheimer's Diseases", Aug. 15, 2015, Publisher: Medicine and Public Health, China Doctoral Dissertations.

* cited by examiner

*Primary Examiner* — Ganapathy Krishnan
(74) *Attorney, Agent, or Firm* — Suzannah K. Sundby, Esq.; Canady + Lortz LLP

(57) ABSTRACT

Provided are a series of crocins compounds and related pharmacological applications thereof in prevention and treatment of Alzheimer's disease. The series of crocins compounds are obtained by taking the Chinese herb, namely *Gardenia jasminoides* Ellis, as a raw material and separating same by means of various methods. The compounds playing a role in preventing oxidative injury caused by hydrogen peroxide ($H_2O_2$) and excitatory amino acid injury caused by L-glutamic acid are screened out by in-vitro cell experiments. The results show that the crocins compounds have good effect in preventing cell injury caused by $H_2O_2$ and L-glutamic acid. The compounds have good effect in preventing and treating Alzheimer's disease due to the fact that significant rise of oxidative stress and excitatory amino acid is a key factor for nerve injury in Alzheimer's disease, and have broad development and application prospect.

3 Claims, No Drawings

CROCINS COMPOUNDS AND USES THEREOF

TECHNICAL FIELD

The present disclosure relates to a series of crocin-like compounds (crocins compounds) and pharmacological application thereof in preventing and treating Alzheimer's disease.

BACKGROUND ART

Crocins are a class of water-soluble carotenoids with a unique structure, include crocetin and glycosyl esters formed by its binding with different glycosyl groups, and are a common pigment ingredient in *Crocus sativus* L. and *Gardenia jasminoides* Ellis. In traditional applications, *Crocus sativus* L. is widely used in Europe and Asia as a good gynecological medicine, and *gardenia* yellow pigments are mostly used as a natural colorant. Many researches in recent years reveal that *Crocus sativus* L. Extracts (CSE), *gardenia* yellow pigments, and monomer ingredients, including crocin digentiobioside (crocin-1) and crocetin manifest efficient pharmacological activities with low toxicity in central nervous system protection[1-4] cardiocerebral vascular system protection[5-6], malignant tumor antagonism and so on.

Alzheimer's disease (AD) is a kind of progressive neurodegenerative diseases related to senility and featured by amnesia, cognitive disorder, and personality change. AD is the most common type among senile dementia. An initial symptom of AD patients is amnesia, further developing to deterioration of orientation, comprehension, judgment, and memory. Advanced patients enter a state of full deterioration, with complete loss of intelligence, and increasingly obvious disorder of movement and language, and finally mostly die of secondary infection and failure.

With the aggravation of aging in the world, the morbidity of AD tends to sharply increase year by year, bringing heavy economic and family burdens to society and people in various countries, especially developing countries. Since German doctor Alzheimer described this disease first time in 1906, over more than 100 years up to now, it is internationally accepted that no method or a medicine curing this disease is available. Thus, in cases where there is no ideal therapeutic drug, screening, research and development of anti-senile dementia drugs have a quite broad market prospect and far-reaching social significance.

A significant pathological feature of AD is extracellular deposition of amyloid β-protein (Aβ) and intracellular tangling of polymerized tau proteins in cerebral cortex and hippocampal nerves. At present, most scholars deem that deposition of a lot of Aβ is an indirect cause of attack of AD, and in this process, there are mainly pathological changes such as inflammation and oxidative stress. A lot of researches prove that oxidative stress is an important mechanism for occurrence and development of AD. Therefore, taking inhibition of oxidative damage as a target has become an important approach to looking for an effective means for preventing and treating AD.

Glutamic acid is an endogenous neurotransmitter in cerebral cortex and hippocampal parts. Under normal physiological conditions, glutamic acid adjusts synaptic transmission of the central nervous system, and takes part in all functions in a normal brain, including learning, memorizing, exercising, recognition, and development. However, under a pathological condition, due to various reasons, a content of glutamic acid is increased, and over-activates receptors, thus causing neuron damage, and producing neurotoxicity. More and more researches reveal that abnormal glutamic acid plays an important role in etiology and pathophysiology of many nerve diseases including Alzheimer's disease, cerebral ischemia, schizophrenia and so on. Therefore, a neuroprotective effect can be achieved by antagonizing the neurotoxicity of glutamic acid[10].

CSE has relatively good effects in inhibiting formation of Aβ fibril and resisting oxidation in vitro. A main pigment crocin-1 contained therein at a relatively low dose may inhibit formation of Aβ fibril, indicating that *Crocus sativus* L. and pigments contained therein may inhibit aggregation and deposition of Aβ in human brains, and thus have relevant actives for preventing and treating AD[2]. Crocin-1 may exert the antioxidant effect by increasing a content of glutathione (GSH), inhibiting formation of peroxidized lipid, retaining activity of superoxide dismutase (SOD) and so on, so as to play a protective effect on PC-12 cells[11].

In animal experiments, CSE (30 and 60 mg/kg) can improve learning and memorizing capabilities of normal rats in experiments, and can effectively inhibit memory disorder of rats caused by hyoscyamine[12]. In a randomized double blind trial lasting for 22 weeks, where *Crocus sativus* L. is prepared into capsules and the capsules are used in research of phase II clinical treatment for mild-to-moderate AD, the capsules of *Crocus sativus* L. have equivalent therapeutical effects as a positive drug donepezil, with no significant difference from the positive drug in adverse drug reactions, and with reduced side effect of nausea induction[3]. In a research of phase II clinical treatment for mild-to-moderate AD, patients in an experiment group are administered with the capsule at 30 mg/day, patients in a control group are administered with a positive control drug memantine at 30 mg/day, and results reveal that therapeutical effects in experiment group which are equivalent to those in the control group are obtained, without significant adverse effects[4].

REFERENCES

[1] Karakani A.-M., Riazi G., Mahmood G.-S., et al. Inhibitory effect of corcin on aggregation of 1 N/4R human tau protein in vitro [J]. *Iranian journal of basic medical sciences*. 2015, 18(5), 485-92.

[2] Papandreou M.-A., Kanakis C.-D., Polissiou M.-G., et al. Inhibitory Activity on Amyloid-β Aggregation and Antioxidant Properties of *Crocus sativus* Stigmas Extract and Its Crocin Constituents [J]. *Journal of Agriculture and Food Chemistry*. 2006, 54(23), 8762-8768.

[3] Akhondzadeh S., Sabet M.-S., Harirchian M.-H., et al. A 22-week, multicenter, randomized, double-blind controlled trial of *Crocus sativus* in the treatment of mild-to-moderate Alzheimer's disease [J]. *Psychopharmacology*. 2010, 207(4), 637-643.

[4] Farokhnia M., Shafiee S.-M., Iranpour N., et al. Comparing the efficacy and safety of *Crocus sativus* L. With memantine in patients with moderate to severe Alzheimer's disease: a double-blind randomized clinical trial [J]. *Human Psychopharmacology*. 2014, 29(4), 351-359.

[5] Zheng Y.-Q., Liu J.-X., Wang J.-N., et al. Effects of crocin on reperfusion-induced oxidative_nitrative injury to cerebral microvessels after global cerebral ischemia [J]. *Brain Research*. 2007, 1138, 86-94.

[6] Higashino S., Sasaki Y, Giddings J.-C., et al. Crocetin, a Carotenoid from *Gardenia jasminoides* Ellis, Protects against Hypertension and Cerebral Thrombogenesis in Stroke-prone Spontaneously Hypertensive Rats [J]. *Phytotherapy Research.* 2014, 28(9), 1315-1319.

[7] Shengyu Dong, Fumei Liu, Xiangyong Li. The Proliferation and Migration Inhibition and Mechanism of Crocin on CNE2 Cells [J]. *Journal of Hubei University for Nationalities•Medical Edition.* 2013, 30(2), 6-12.

[8] Xinxing Wang, Zhenghong Yu, Shulu Shi et al. The Inhibitory Effects and Mechanisms of Crocin on Human Lung Adenocarcinoma Cell Line (SPC-A1) [J]. *Chinese Clinical Oncology.* 2013, 18(4), 295-299.

[9] Fuxiong Chen, Jia Tao, Sui Huang, et al. Clinical Research and Virological Features of Epstein-Barr Virus Associated Infectious Mononucleosis and EBV-AHS [A]. Chinese Medical Association, Chinese Pediatric Society. *Compilation of papers on 17th National Pediatric Academic Conference of Chinese Medical Association* (volume 1) [C]. Chinese Medical Association, Chinese Pediatric Society: 2012: 1

[10] Lau A., Tymianski M. Glutamate receptors, neurotoxicity and neurodegeneration [J]. *European Journal of Physiology.* 2010, 460(2), 525-542.

[11] Ochiai T., Ohno S., Soeda S., et al. Crocin prevents the death of rat pheochromyctoma (PC-12) cells by its antioxidant effects stronger than those of a-tocopherol [J]. *Neuroscience Letters.* 2004, 362(1), 61-64.

[12] Pitsikas N., Sakellaridis N. *Crocus sativus* L. extracts antagonize memory impairments in different behavioural tasks in the rat [J]. *Behavioural Brain Research.* 2006, 173(1), 112-115.

SUMMARY

The present disclosure relates to following technical solutions.

[1] A crocin-like compound represented by a general formula (I) or a pharmaceutically acceptable salt thereof,

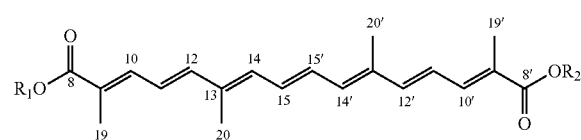

(I)

wherein configuration of a double bond between positions 13 and 14 is trans E or cis Z, $R_1$ and $R_2$ are each independently selected from the group consisting of H, $CH_3$, $CH_2CH_3$, a glycosyl group and a quinic acid group, a basic structure of quinic acid is:

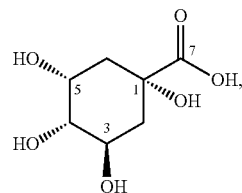 [SMILES: O=C(O)[C@]1(O)C[C@@H](O)[C@@H](O)[C@H](O)C1]

wherein after hydrogen is removed from hydroxyl groups at positions 1, 3, 4, 5 and/or 7, different quinic acid groups may be formed, for example, common quinic acid groups with removal of hydrogen at position 3 or position 5 may be expressed as:

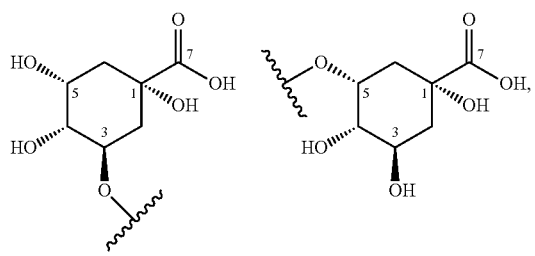 [SMILES: *O[C@@H]1C[C@](O)(C(=O)O)C[C@@H](O)[C@H]1O ; *O[C@@H]1C[C@@](O)(C(=O)O)C[C@@H](O)[C@@H]1O]

the glycosyl group is selected from the group consisting of glucosyl, gentiobiosyl, xylosyl, galactosyl, mannosyl, arabinosyl, rhamnosyl, ribosyl, lyxosyl and fucosyl groups, the number of the glycosyl group is 0-2, one or more of hydroxyl group of the glycosyl group may be acylated by acylation groups of sinapoyl, caffeoyl, coumaroyl, cinnamoyl, $CH_3(CH_2)_nCO$ or $HOOC(CH_2)_nCO$, one or more of hydroxyl group at positions 3, 4 and/or 5 of the quinic acid group may be acylated by acylation groups of sinapoyl, caffeoyl, coumaroyl, cinnamoyl, $CH_3(CH_2)_nCO$ or $HOOC(CH_2)_nCO$, and a carboxyl group at position 1 of the quinic acid group may be esterified with methyl or ethyl group, wherein the compound of the general formula (I) includes none of following compounds:

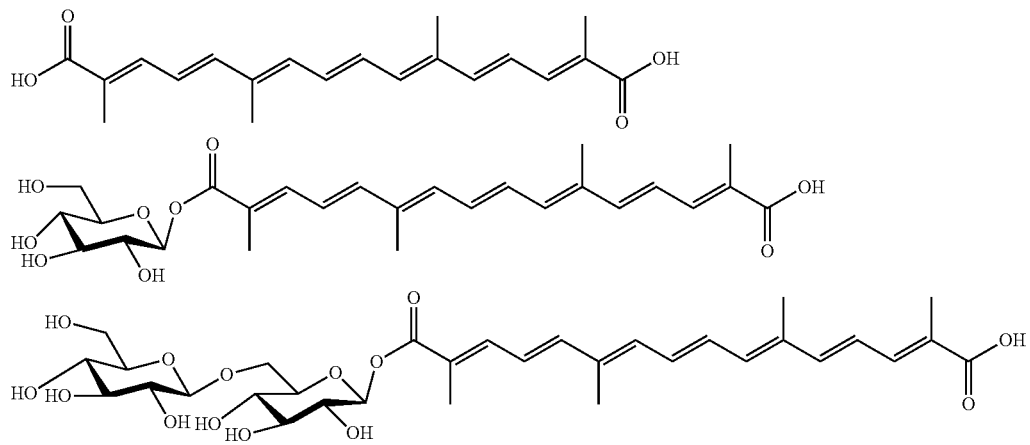

-continued
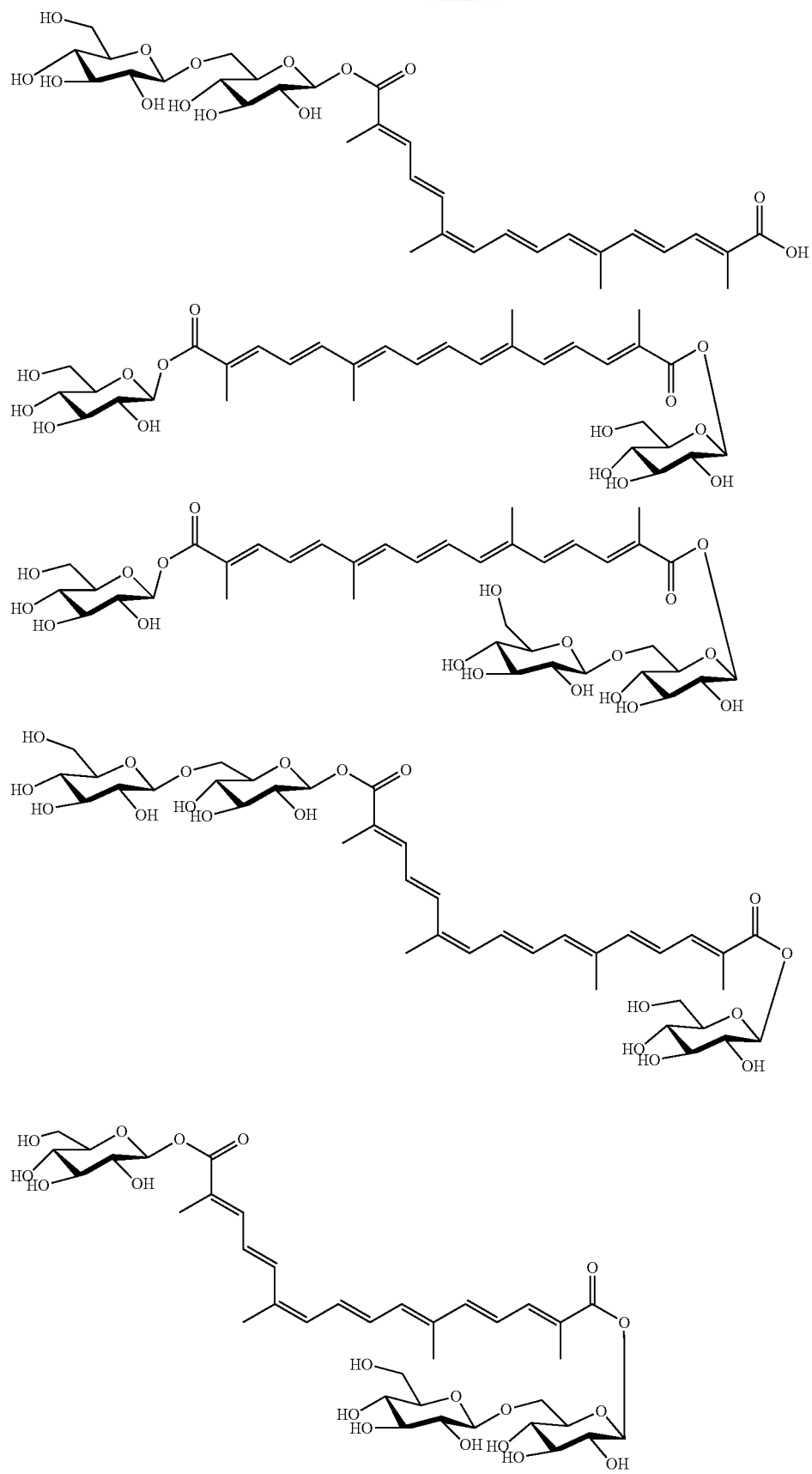

-continued
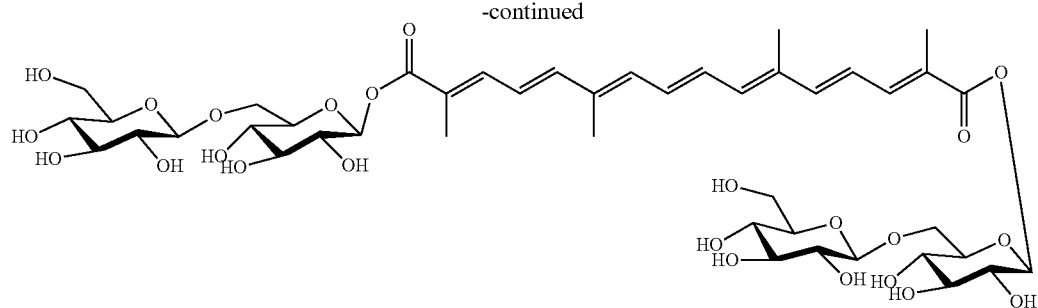
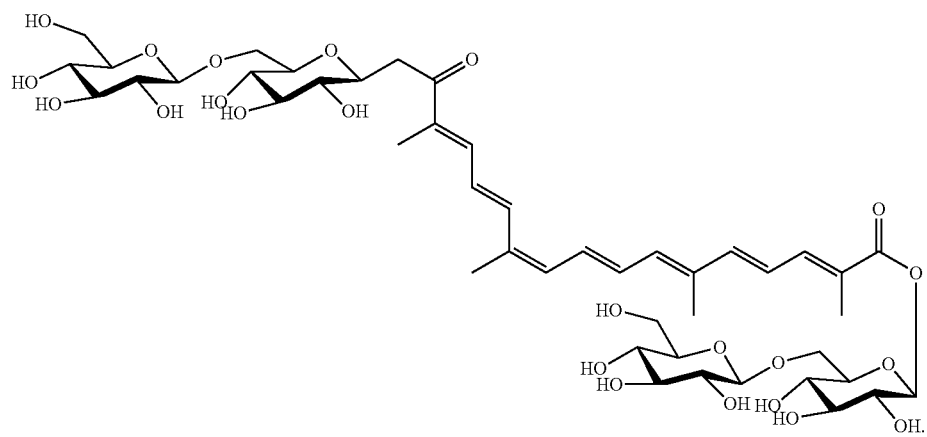
[2] The compound according to item [1], wherein the configuration of the double bond between the positions 13 and 14 is trans E configuration, $R_1$ represents glucosyl group, and $R_2$ represents a quinic acid group.
[3] The compound according to item [2], wherein the compound is
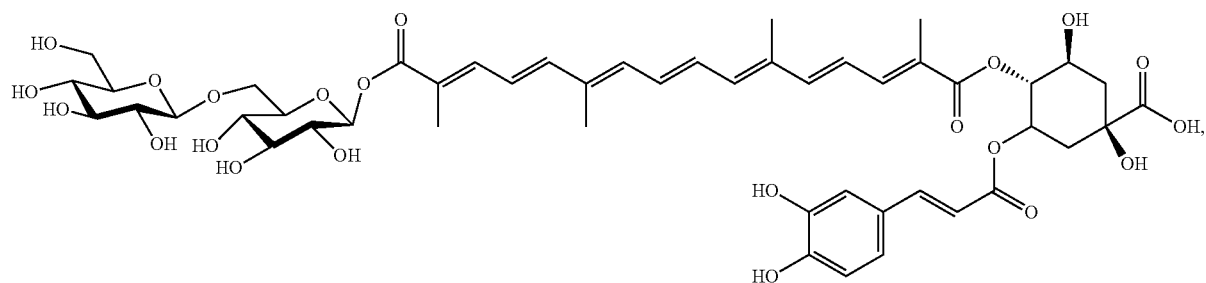
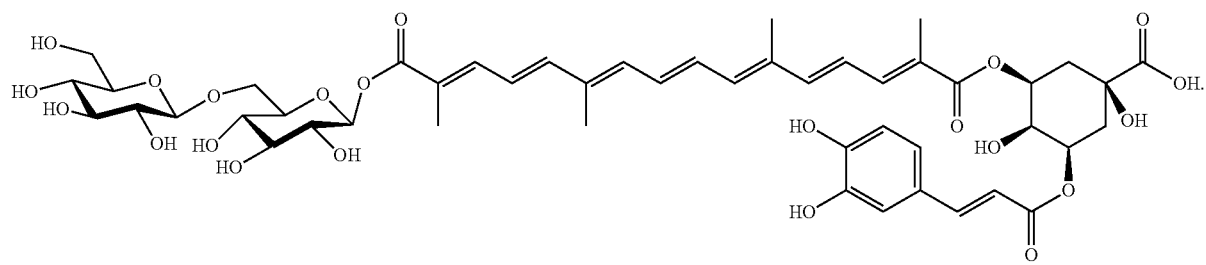

[4] The compound according to Item [1], wherein the configuration of the double bond between the positions 13 and 14 is cis Z configuration, $R_1$ represents H, glucosyl group or a quinic acid group, and $R_2$ represents H, glucosyl group or a quinic acid group.
[5] The compound according to item [4], wherein the compound is
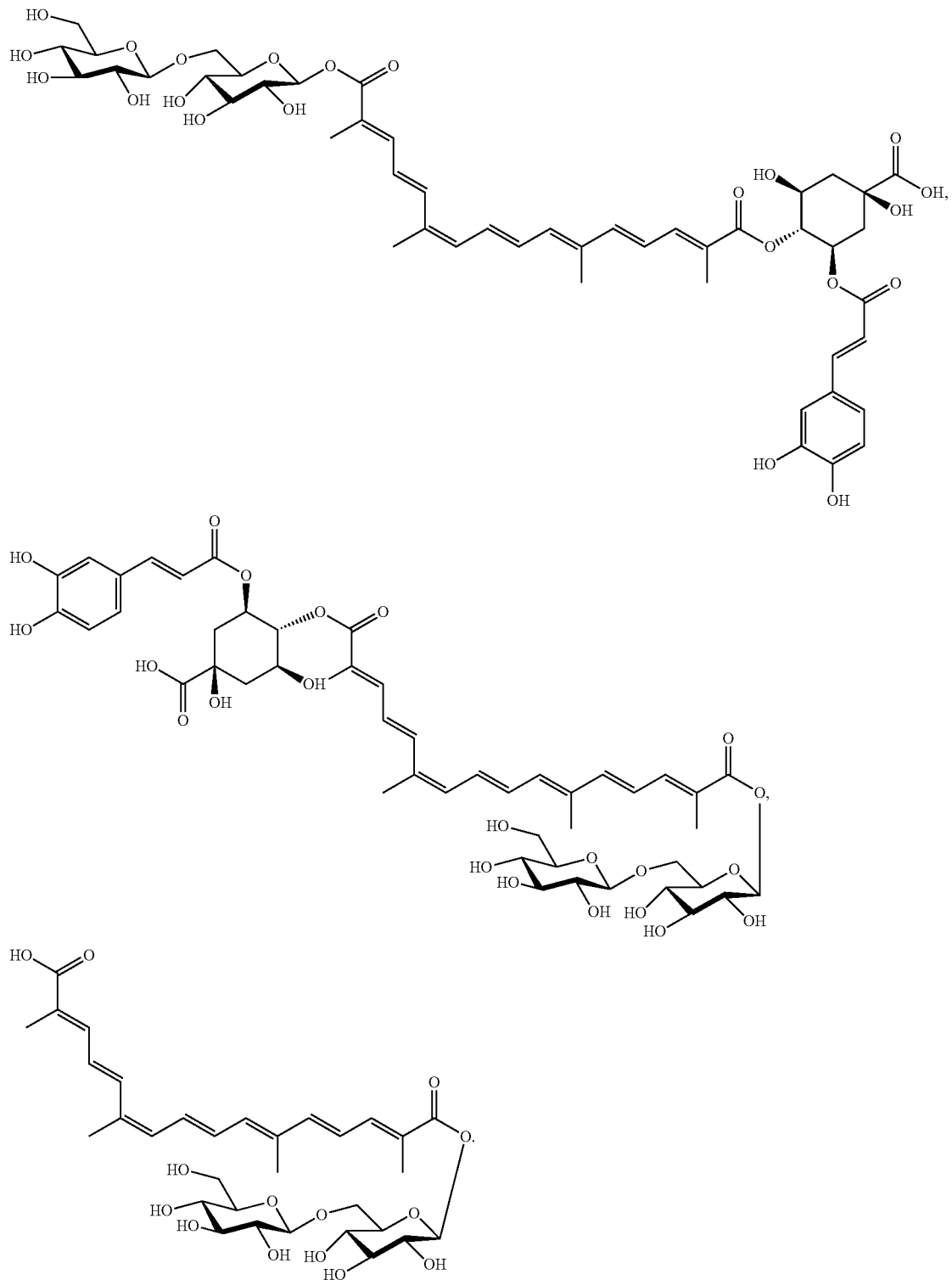

[6] The compound according to item [1], wherein the configuration of the double bond between the positions 13 and 14 is trans E configuration, $R_1$ represents glucosyl group, and $R_2$ represents glucosyl group or H.

[7] The compound according to item [6], wherein the compound is

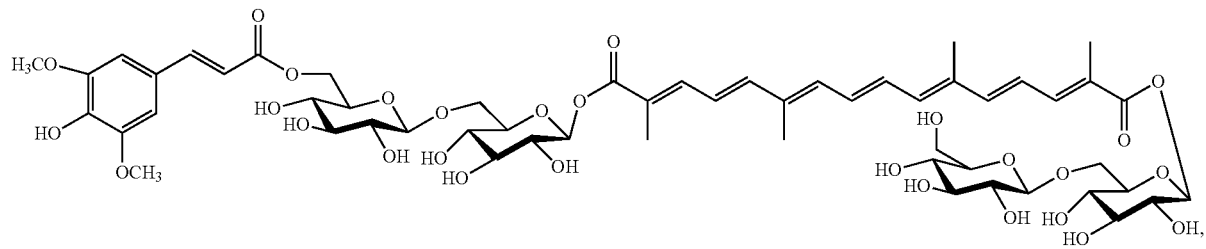

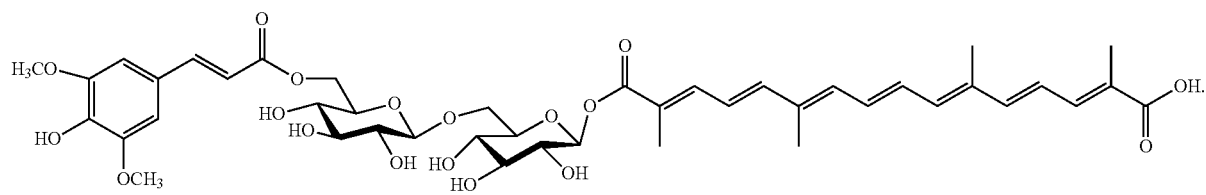

30

[8] The compound according to item [1], wherein the configuration of the double bond between the positions 13 and 14 is trans E configuration, $R_1$ represents glucosyl group, and $R_2$ represents $CH_2CH_3$.

[9] The compound according to item [8], wherein the compound is

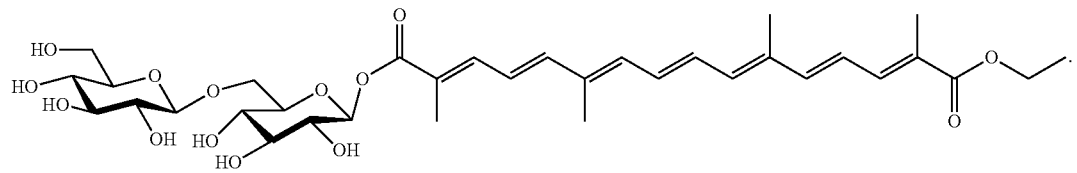

[10] The compound according to item [1], wherein the configuration of the double bond between the positions 13 and 14 is trans E configuration, $R_1$ represents glucosyl group or xylosyl group, and $R_2$ represents H.

[11] The compound according to item [10], wherein the compound is

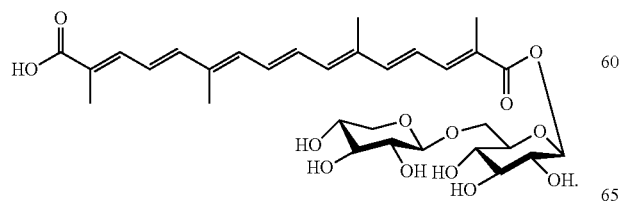

[12] A crocin-like compound, a structural formula thereof being

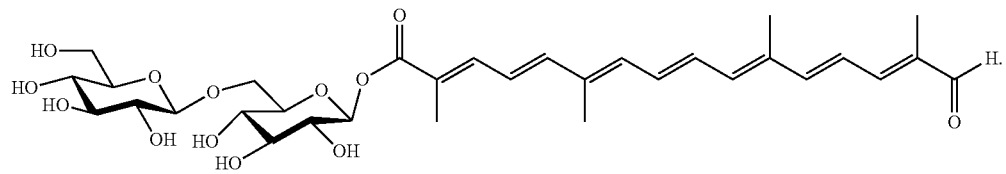

[13] Use of the compound according to any one of items [1] to [12] in preparation of a pharmaceutical for preventing and treating neurodegenerative diseases.

[14] The use according to item [13], the neurodegenerative diseases including vascular dementia, vascular cognitive disorder, Alzheimer's disease, memory decline, brain tissue degenerative lesion syndromes or cholinergic neurodegenerative lesion.

[15] A composition, the composition including the compound according to any one of items [1] to [12] and other crocin-like compounds, the other crocin-like compounds being selected from the group consisting of the followings:

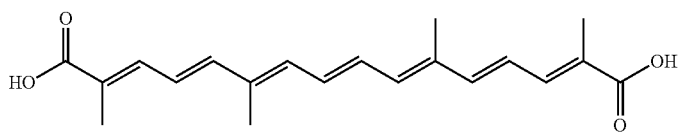

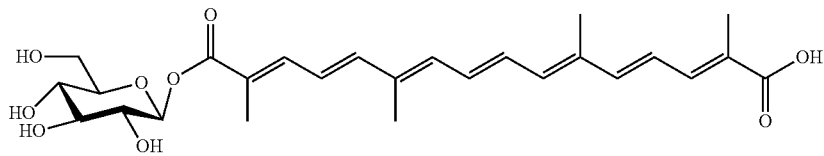

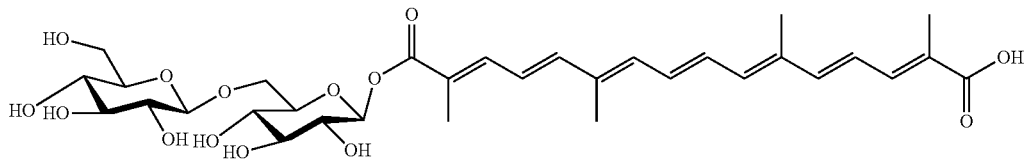

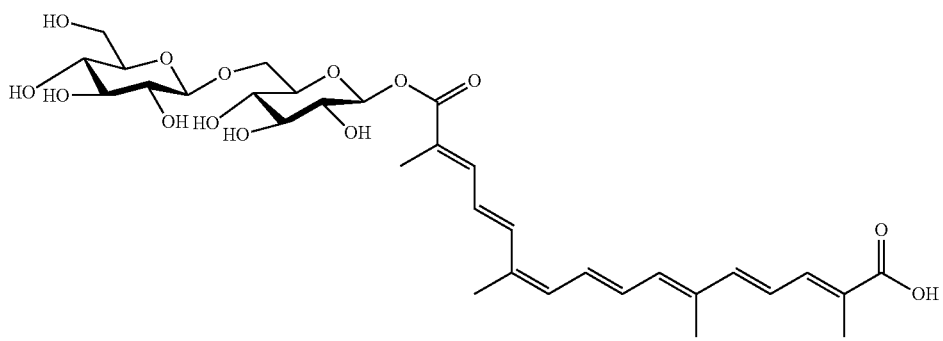

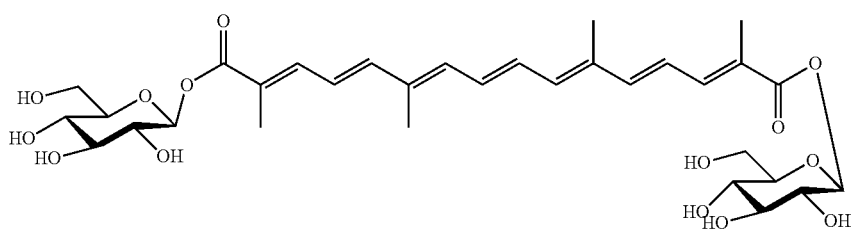

-continued
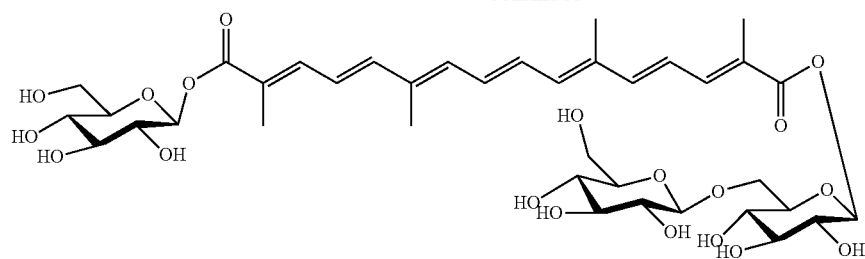
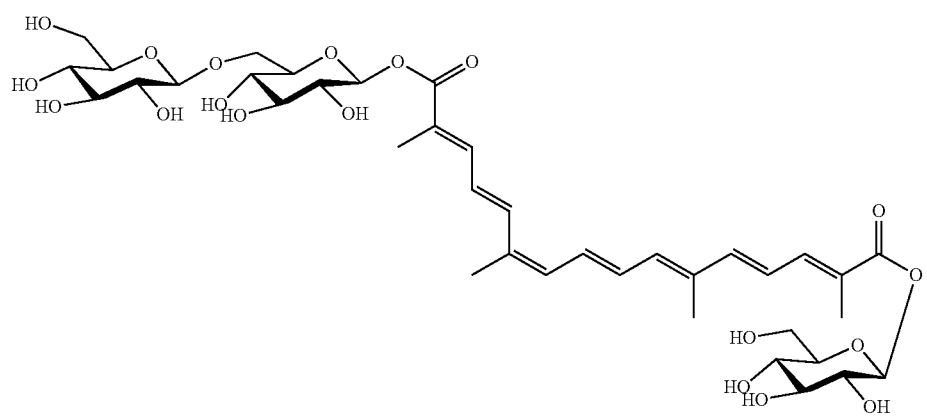
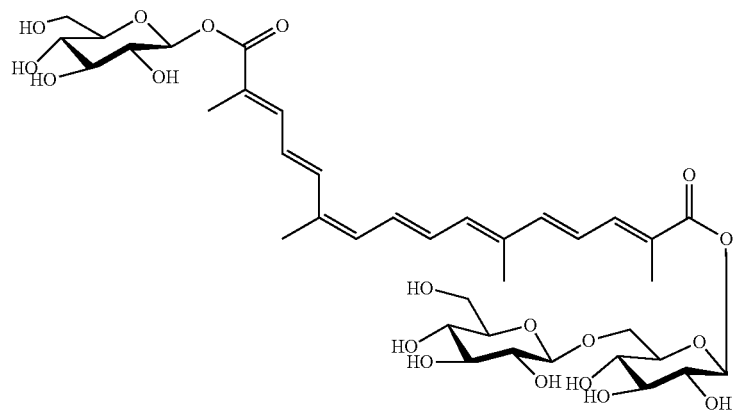
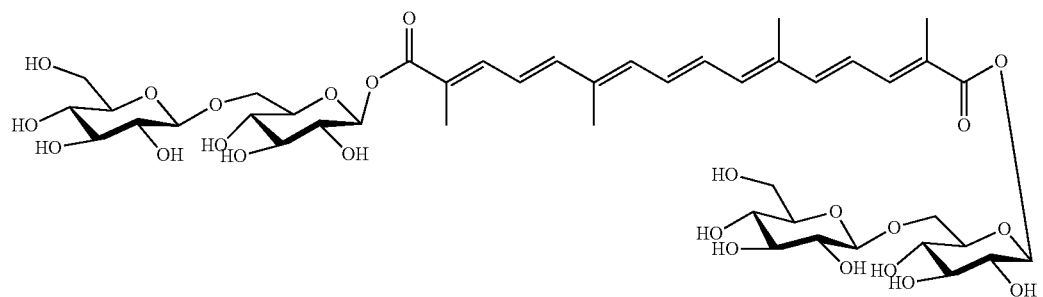

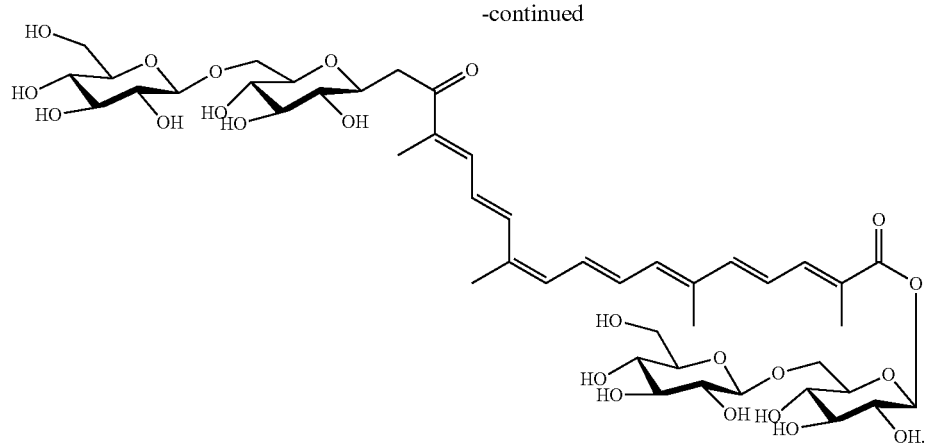

[16] A pharmaceutical composition, the pharmaceutical composition including the compound according to any one of items [1] to [12] and pharmaceutical carriers.

[17] A method for preparing the compound according to any one of items [1] to [12], the method including: taking a Chinese herb *Gardenia jasminoides* Ellis as a raw material, and extracting the same by hot extraction or ultrasonic extraction with ethanol, methanol or water for different extracting times and periods, concentrating extract solutions under a reduced pressure to obtain a total extract of *Gardenia jasminoides* Ellis.

[18] The method according to item [17], wherein the total extract of *Gardenia jasminoides* Ellis is dissolved in a suitable amount of water and centrifuged, a supernatant is subjected to macroporous adsorption resin open column chromatography, a suitable column bed volume of water and/or 30%-95% ethanol is used for elution, an eluate is collected, and concentrated under a reduced pressure to obtain an active fraction of crocins of *Gardenia jasminoides* Ellis, and various column chromatographies are carried out for further separation.

[19] The method according to item [17], wherein heating reflux extraction is carried out 3 times with 4 times amount of 60% ethanol, 2 hours at each time.

[20] The method according to item [18], wherein a gradient elution is carried out with water, and then sequentially with 30% ethanol, 50% ethanol, 70% ethanol, and 95% ethanol, each 4 column bed volumes, followed by concentrating an eluate of the 70% ethanol under a reduced pressure, to obtain the active fraction of crocins of *Gardenia jasminoides* Ellis.

[21] The method according to item [18], wherein the column chromatography includes silica gel column chromatography, ODS open column chromatography, Sephadex LH-20 open column chromatography, and Pre-HPLC column chromatography.

DETAILED DESCRIPTION OF EMBODIMENTS

Inventors of the present disclosure extracted a series of novel crocin-like compounds represented by a general formula (I) from a Chinese herb *Gardenia jasminoides* Ellis by multiple chemical means, and upon identification through multiple spectroscopic methods and cell experiments, it was proved that these crocin-like compounds have excellent protection effects on a central nervous system.

General Formula (I)

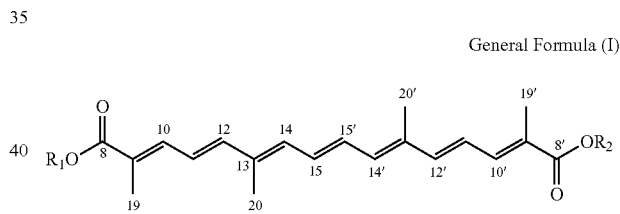

Various substituents are defined as in the preceding.

In a first group of preferred compounds, a position 13-14 is of trans E configuration, $R_1$ represents glucosyl group, and $R_2$ represents a quinic acid group.

In the above, when $R_1$ represents Glc-(1→6)-Glc (gentiobiosyl) group, and $R_2$ represents a 3-O-caffeoylquinic acid-4-oxy group, a new compound neocrocin B is obtained, referred to as GJ-1 for short.

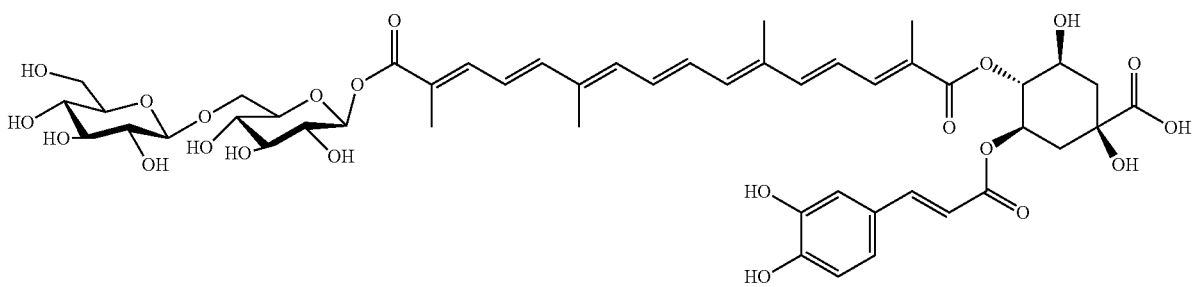

In the above, when $R_1$ represents gentiobiosyl group, and $R_2$ represents a 3-O-caffeoylquinic acid-5-oxy group, a new compound neocrocin C is obtained, referred to as GJ-2 for short.

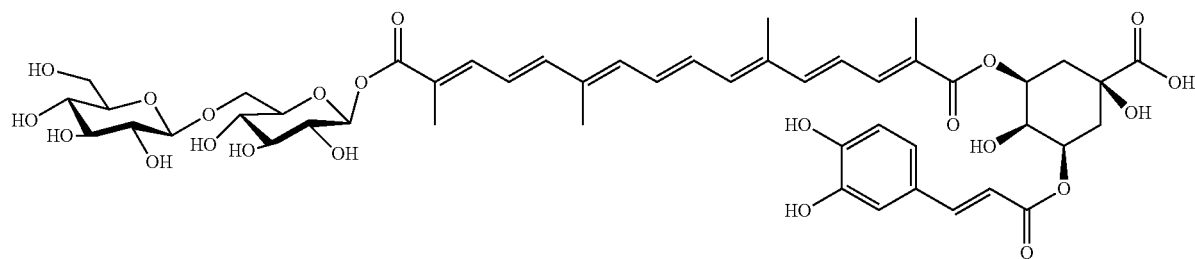

In a second group of preferred compounds, a position 13-14 is of cis Z configuration, $R_1$ represents H, glucosyl group or a quinic acid group, and $R_2$ represents glucosyl group or a quinic acid group.

In the above, when $R_1$ represents gentiobiosyl group, and $R_2$ represents a 3-O-caffeoylquinic acid-4-oxy group, a new compound neocrocin D is obtained, referred to as GJ-3 for short.

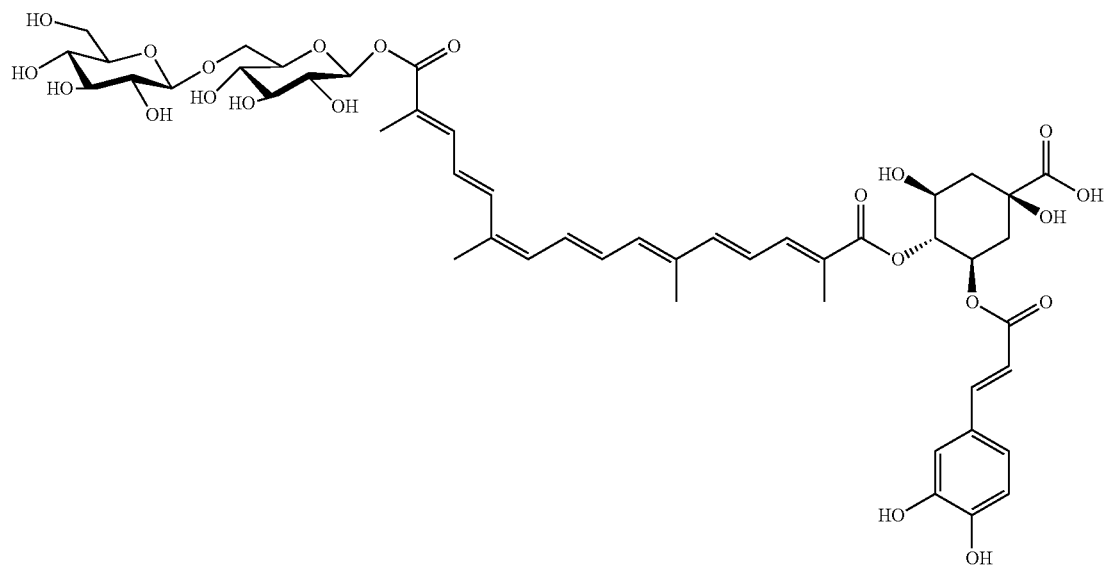

In the above, when $R_1$ represents a 3-O-caffeoylquinic acid-4-oxy group, and $R_2$ represents gentiobiosyl group, a new compound neocrocin E is obtained, referred to as GJ-4 for short.

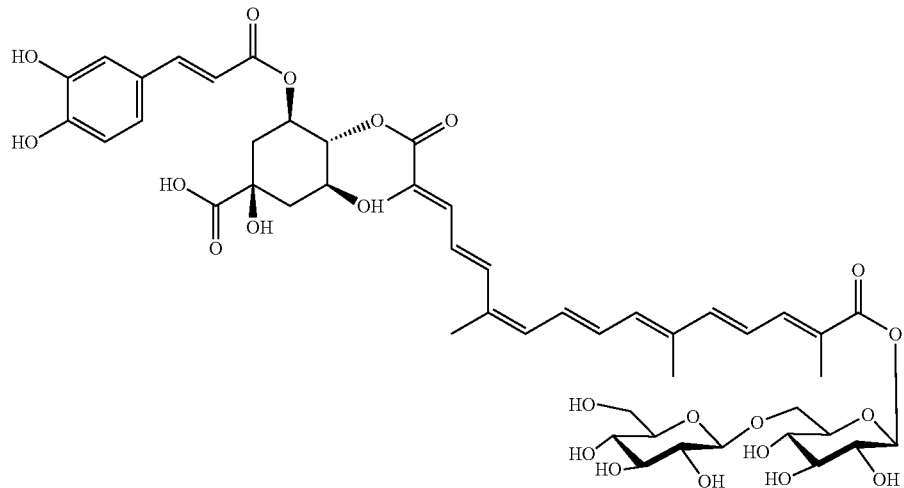

In the above, when $R_1$ represents H, and $R_2$ represents gentiobiosyl group, a new compound named as 13Z-crocetin-8'-O-β-D-gentiobioside is obtained, referred to as GJ-5 for short.

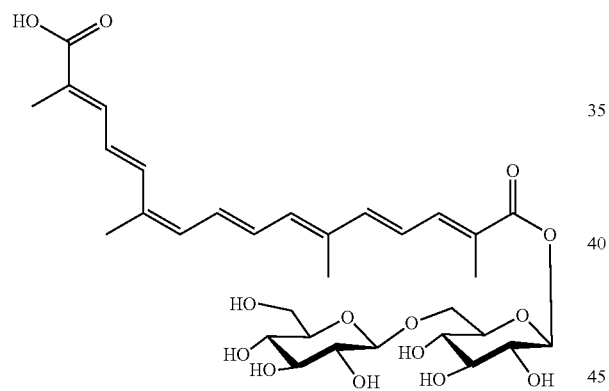

In a third group of preferred compounds, a position 13-14 is of trans E configuration, $R_1$ represents glucosyl group, and $R_2$ represents glucosyl group or H.

In the above, when $R_1$ represents a 6-O-trans-sinapoyl gentiobiosyl group, and $R_2$ represents gentiobiosyl group, a new compound neocrocin G is obtained, referred to as GJ-6 for short.

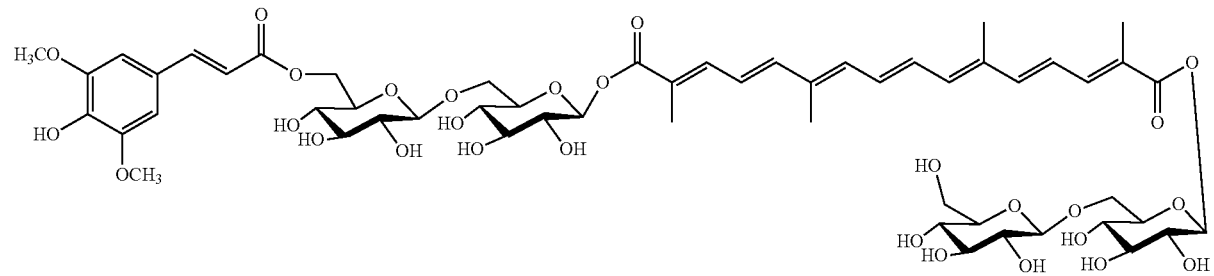

In the above, when $R_1$ represents a 6-O-trans-sinapoyl gentiobiosyl group, and $R_2$ represents H, a new compound neocrocin F is obtained, referred to as GJ-7 for short.

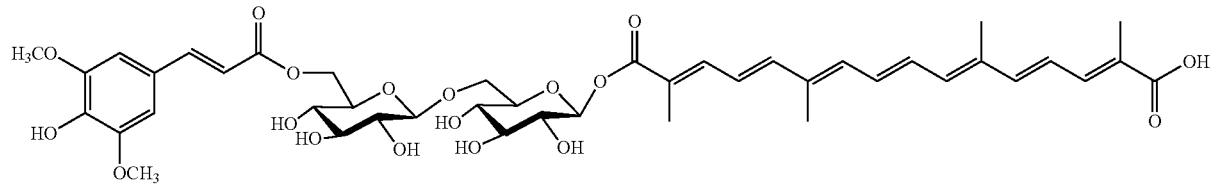

In a fourth group of preferred compounds, a position 13-14 is of trans E configuration, $R_1$ represents glucosyl group, and $R_2$ represents $CH_2CH_3$.

In the above, when $R_1$ represents a gentiobiosyl group, and $R_2$ represents $CH_2CH_3$, a new compound neocrocin H is obtained, referred to as GJ-8 for short.

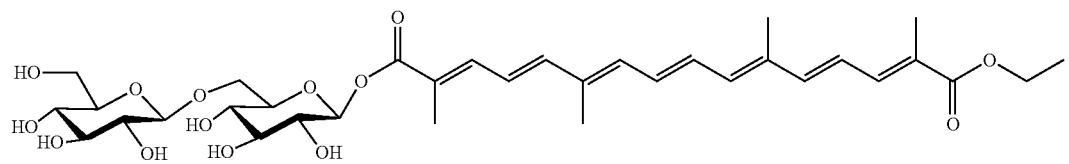

A fifth group of preferred compound is neocrocin I, referred to as GJ-9 for short.

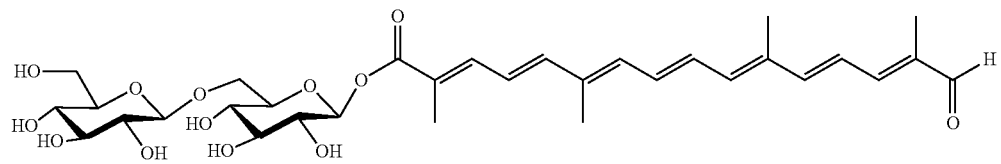

In a sixth group of preferred compounds, position 13-14 is of trans E configuration, $R_1$ represents glucosyl group or xylosyl group, and $R_2$ represents H.

In the above, when $R_1$ represents H, and $R_2$ represents xylosyl-(1→6)-glucosyl group, a new compound neocrocin J is obtained, referred to as GJ-10 for short.

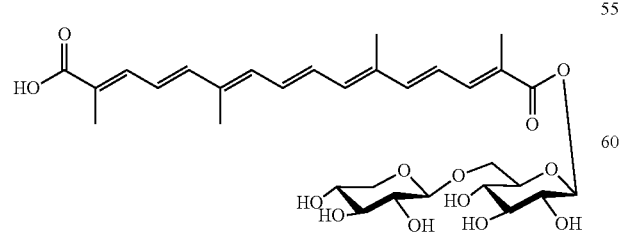

Besides, compounds listed in following Table 1 within the range of the general formula (I) are known.

TABLE 1

| Abbreviation | Chemical formula structure |
|---|---|
| GJ-11 | |
| GJ-12 | |
| GJ-13 | |
| GJ-14 | |
| GJ-15 | |
| GJ-16 | |

TABLE 1-continued

| Abbreviation | Chemical formula structure |
| --- | --- |
| GJ-17 | |
| GJ-18 | |
| GJ-19 | |
| GJ-20 | |

EXAMPLES

Example 1: Extraction and Separation of Ingredients of Crocins in *Gardenia jasminoides* Ellis 40.0 Kg of dry and mature fruits of *Gardenia jasminoides* Ellis were taken, smashed in a suitable manner, and extracted under heating and reflux 3 times with 4 times amount of 60% ethanol, 2 hours at each time. Extract solutions were combined, and a solvent was removed under a reduced pressure, to obtain 6.2 kg of a total extract of *Gardenia jasminoides* Ellis (with a yield of 15.5%). The extract was dissolved in a suitable amount of water, and centrifuged, a supernatant was subjected to macroporous resin open column chromatography (20.0×90 cm), and gradient elution subsequently with water, 30% ethanol, 50% ethanol, 70% ethanol, and 95% ethanol at 4 times a column bed volume. And eluates in various fractions were collected, and solvents were recovered respectively under a reduced pressure, to obtain about 4.5 kg of a combined fraction from water elution and 30% ethanol elution, 710.0 g of fraction from 50% ethanol elution, 150.0 g of fraction from 70% ethanol elution, and 112.0 g of fraction from 95% ethanol elution, wherein the fraction from 70% ethanol elution is just an active fraction of crocins of *Gardenia jasminoides* Ellis.

150 g of fraction from 70% ethanol elution was subjected to silica gel column chromatography (φ7×60 cm), and gradient elution with 99:1-6:4:0.8 chloroform-methanol-water, to separate out compounds GJ-11 (49.1 mg), GJ-12 (136.5 mg), and GJ-13 (7.0 g), respectively.

A silica gel sub-fraction Fr. 9 was subjected to ODS column chromatography, and gradient elution with 30%-70% methanol-water to separate out a compound GJ-19 (545.1 mg), subjected to HPLC and elution with 60% methanol-water to obtain a compound GJ-20 (265.7 mg), subjected to HPLC and elution with 68% methanol-acid water solution (0.1% acetic acid) to obtain a compound GJ-1 (120.0 mg) and 104.8 mg of a mixture of GJ-3 and GJ-4 (mixed by 1:2). And further, compounds GJ-3 and GJ-4 were separated using water (0.3% TEAA):acetonitrile=55:45.

A silica gel sub-fraction Fr. 7 was subjected to ODS column chromatography and gradient elution with 40%-80% methanol-water to separate out a compound GJ-11 (16.0 mg), subjected to HPLC and elution with 55% methanol-acid water solution (0.1% acetic acid) to obtain a compound GJ-2 (6.3 mg), subjected to HPLC and elution with 42% acetonitrile-acid water solution (0.1% acetic acid) to obtain a compound GJ-13 (8.0 mg) and a compound GJ-5 (16.0 mg).

A silica gel sub-fraction Fr. 8 was subjected to ODS column chromatography and gradient elution with 55%-65% methanol-water to separate out a compound 16 (143.7 mg), subjected to HPLC and elution with 55% methanol-acid water solution (0.1% acetic acid) to obtain a compound GJ-6 (59.1 mg) and GJ-2 (21.9 mg), subjected to HPLC and elution with 68% methanol-acid water solution (0.1% acetic acid) to obtain a compound GJ-1 (400.9 mg), subjected to HPLC and elution with 32% acetonitrile-acid water solution (0.1% acetic acid) to obtain a compound GJ-17 (1.8 mg) and GJ-18 (3.5 mg).

A silica gel sub-fraction Fr. 6 was subjected to ODS column chromatography and gradient elution with 50%-90% methanol-water to separate out a compound GJ-15 (315.7 mg), subjected to HPLC and elution with 60% methanol-acid water solution (0.1% acetic acid) to obtain a compound GJ-10 (10.0 mg), subjected to HPLC and elution with 65% methanol-acid water solution (0.1% acetic acid) to obtain a compound GJ-9 (2.0 mg) and GJ-7 (66.2 mg), subjected to HPLC and elution with 70% methanol-acid water solution (0.1% acetic acid) to obtain a compound GJ-8 (10.0 mg).

Structure information of the compounds obtained is listed in Table 2.

TABLE 2

| NO | Serial No. | Structure |
|---|---|---|
| 1* | GJ-1 | 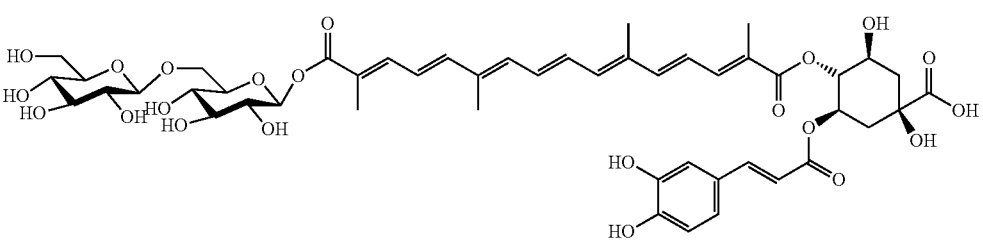 |
| 2* | GJ-2 | 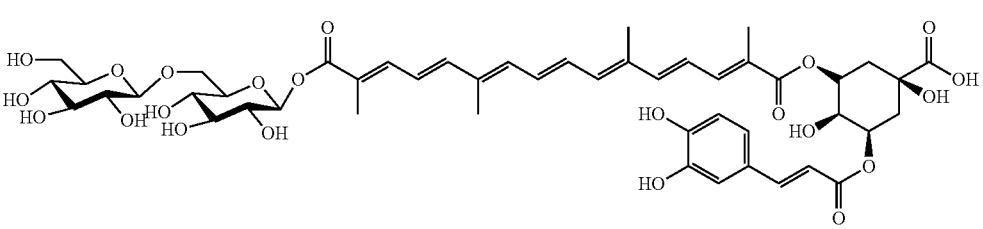 |

TABLE 2-continued
| NO | Serial No. | Structure |
|---|---|---|
| 3* | GJ-3 | 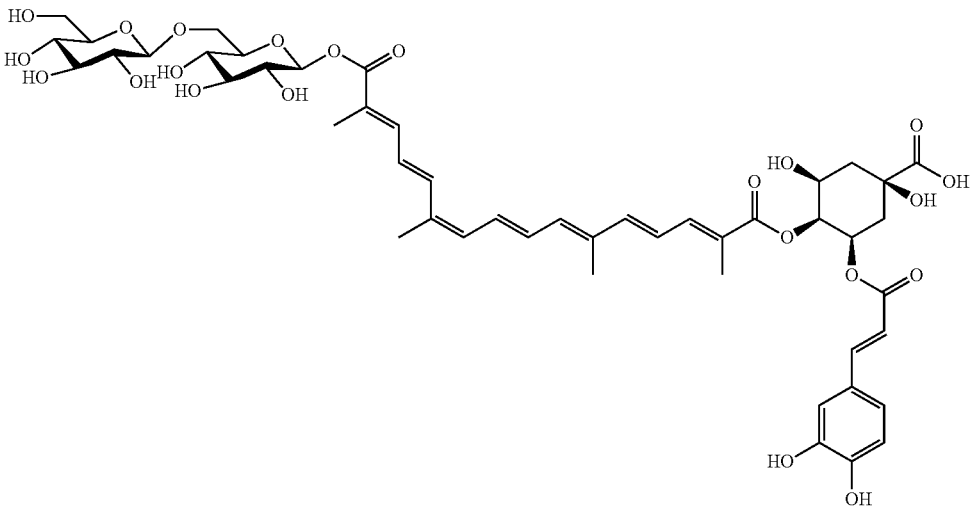 |
| 4* | GJ-4 | 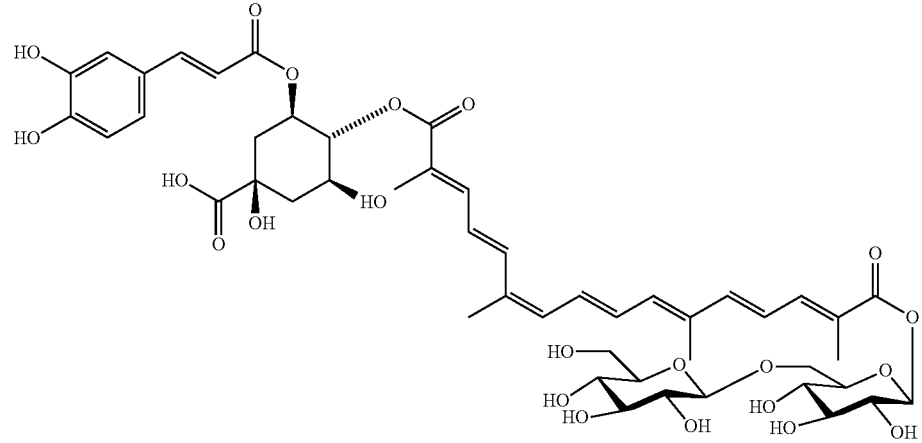 |
| 5* | GJ-5 | 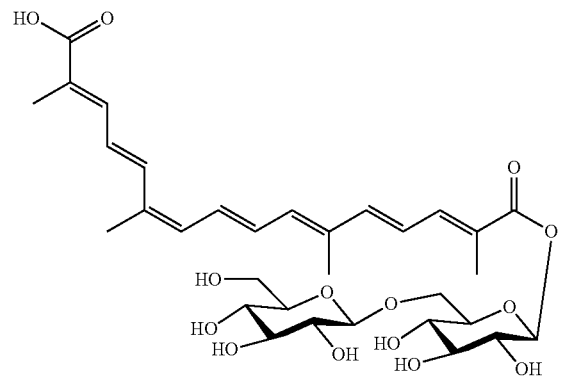 |
| 6* | GJ-6 | 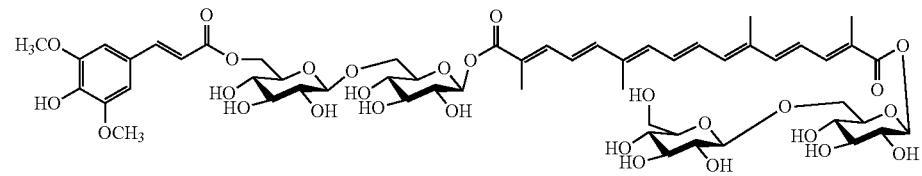 |

TABLE 2-continued

| NO | Serial No. | Structure |
|---|---|---|
| 7* | GJ-7 | 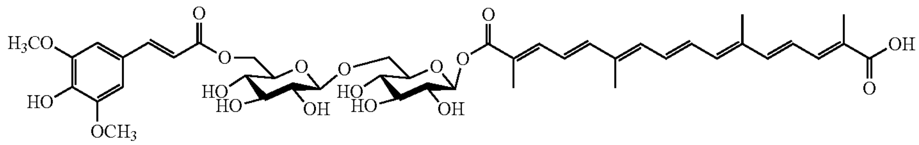 |
| 8* | GJ-8 | 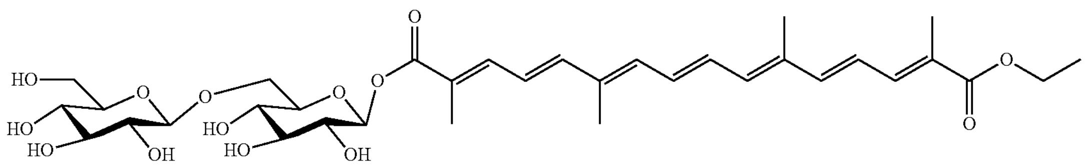 |
| 9* | GJ-9 | 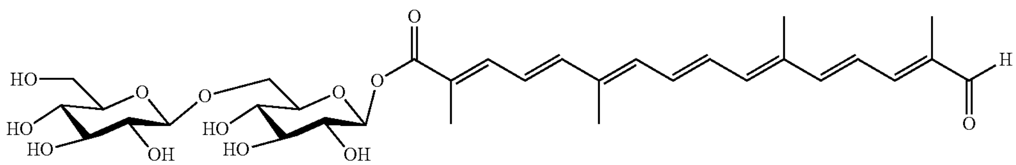 |
| 10* | GJ-10 | 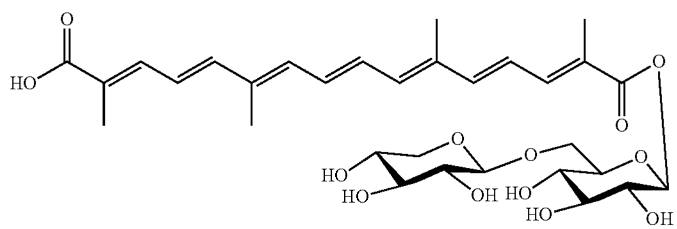 |
| 11 | GJ-11 | 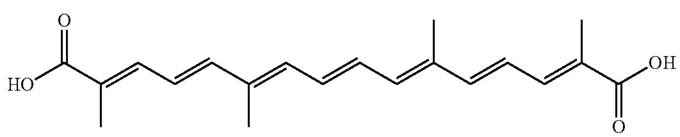 [SMILES: CC(/C=C/C=C(\C)C(=O)O)=C\C=C\C=C(C)\C=C\C=C(/C)C(=O)O] |
| 12 | GJ-12 | 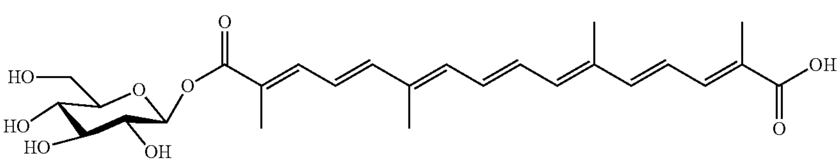 |
| 13 | GJ-13 | 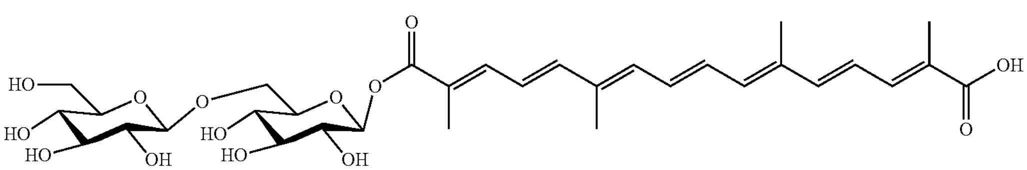 |
| 14 | GJ-14 | 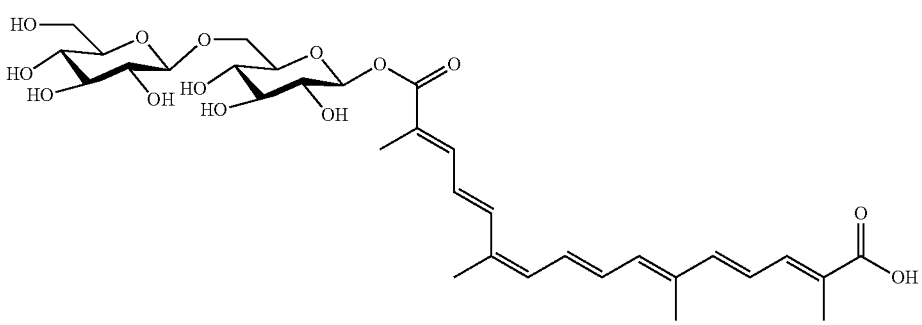 |

TABLE 2-continued
| NO | Serial No. | Structure |
|---|---|---|
| 15 | GJ-15 | 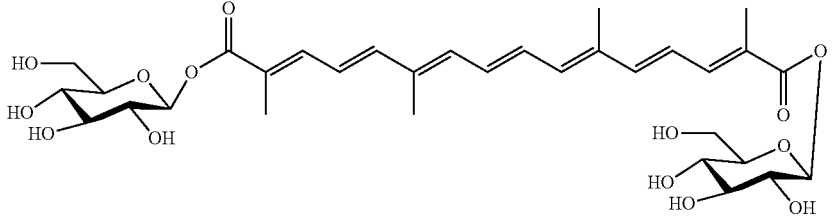 |
| 16 | GJ-16 | 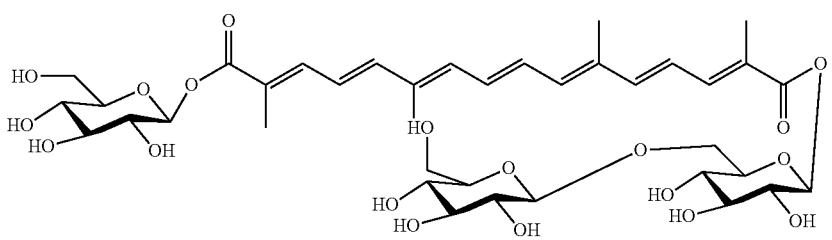 |
| 17 | GJ-17 | 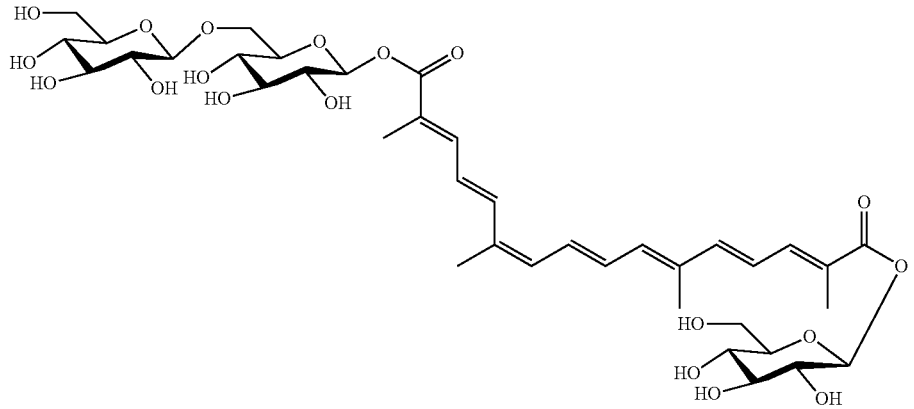 |
| 18 | GJ-18 | 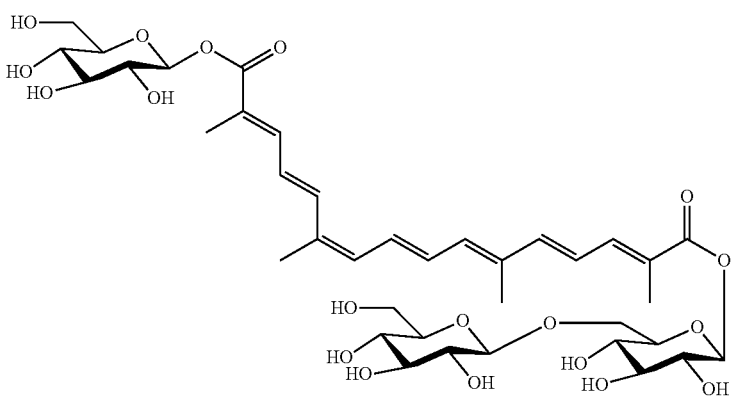 |
| 19 | GJ-19 | 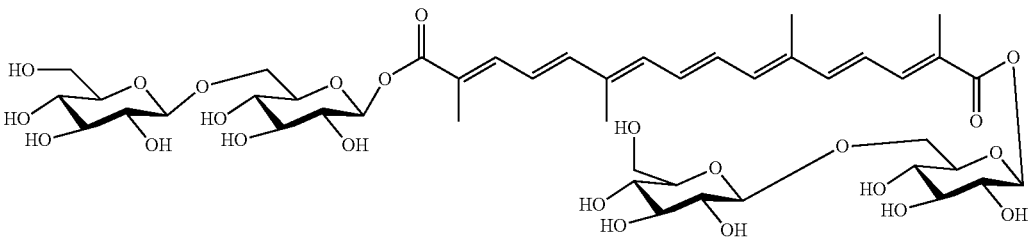 |

TABLE 2-continued

| Serial NO | No. | Structure |
|---|---|---|
| 20 | GJ-20 | (structure) |

Physical and chemical data of the compounds obtained are as follows:

Compound GJ-1: red amorphous powder; ESI-MS (positive): m/z 1011[M+Na]$^+$; HR-ESI-MS: m/z 989.3642[M+H]$^+$ (calcd for $C_{48}H_{61}O_{22}$, 989.3654), confirming a molecular formula of the compound GJ-1 as $C_{48}H_{60}O_{22}$; UV(MeOH)$\lambda_{max}$(log ε): 433 (5.32), 458 (5.28), 331 (4.68), 253 (4.52)nm; IR(KBr)$v_{max}$ 968, 1061, 1224, 1268, 1576, 1610, 1694, 2920, 3401 cm$^{-1}$; see Table 3 for $^{13}$C NMR (DMSO-d$_6$, 150 MHz).

Compound GJ-2: red amorphous powder; ESI-MS (positive): m/z 1011[M+Na]$^+$; HR-ESI-MS: m/z 989.3646[M+H]$^+$ (calcd for $C_{48}H_{61}O_{22}$, 989.3654), confirming a molecular formula of the compound GJ-2 as $C_{48}H_{60}O_{22}$; UV(MeOH)$\lambda_{max}$(log ε): 431 (4.63), 457 (4.56), 331 (4.12), 249 (3.85); IR(KBr)$v_{max}$ 1064, 1230, 1279, 1602, 1698, 2921, 3417 cm$^{-1}$; see Table 3 for $^{13}$C NMR (DMSO-d$_6$ 150 MHz).

Compound GJ-3: red amorphous powder; ESI-MS (positive): m/z 1011[M+Na]$^+$; HR-ESI-MS: m/z 1011.3471[M+Na]$^+$ (calcd for $C_{48}H_{60}O_{22}$Na, 1011.3474), confirming a molecular formula of the compound GJ-3 as $C_{48}H_{60}O_{22}$; UV(MeOH)$\lambda_{max}$(log ε): 429 (5.04), 453 (4.99), 324 (4.68), 251 (4.04)nm; IR(KBr)$v_{max}$ 969, 1062, 1229, 1277, 1607, 1693, 2920, 3368 cm$^{-1}$; see Table 3 for $^{13}$C NMR (DMSO-d$_6$, 150 MHz).

Compound GJ-4: red amorphous powder; ESI-MS (positive): m/z 1011[M+Na]$^+$; HR-ESI-MS: m/z 1011.3471 [M+Na]$^+$ (calcd for $C_{48}H_{60}O_{22}$Na, 1011.3474), confirming a molecular formula of the compound GJ-4 as $C_{48}H_{60}O_{22}$; UV(MeOH)$\lambda_{max}$(log ε): 429 (5.04), 453 (4.99), 324 (4.68), 251 (4.04)nm; IR(KBr)$v_{max}$ 969, 1062, 1229, 1277, 1607, 1693, 2920, 3368 cm$^{-1}$; see Table 3 for $^{13}$C NMR (DMSO-d$_6$, 150 MHz).

Compound GJ-5: red amorphous powder; ESI-MS (positive): m/z 675[M+Na]$^+$, m/z 1327 [2M+Na]$^+$, inferring a molecular weight of the compound GJ-14 as 652; HR-ESI-MS: 675.2617 [M+Na$^+$] (a calculated value is 675.2629), determining a molecular formula of the compound GJ-14 as $C_{32}H_{44}O_{14}$. See Table 3 for $^{13}$C NMR (DMSO-d$_6$, 150 MHz).

Compound GJ-6: red amorphous powder; ESI-MS (positive): m/z 1205 [M+Na]$^+$; HR-ESI-MS: m/z 1183.4479 [M+H]$^+$ (calcd for $C_{55}H_{75}O_{28}$, 1183.4445), confirming a molecular formula of the compound GJ-6 as $C_{55}H_{74}O_{28}$; UV(MeOH)$\lambda_{max}$(log ε): 434 (5.22), 459 (5.17), 330 (4.78), 242 (4.65); IR(KBr)$v_{max}$ 1059, 1119, 1225, 1273, 1610, 1701, 2920, 3385 cm$^{-1}$; see Table 3 for $^{13}$C NMR (DMSO-d$_6$, 150 MHz).

Compound GJ-7: red amorphous powder; ESI-MS (positive): m/z 881 [M+Na]$^+$; HR-ESI-MS: m/z 881.3188 [M+Na]$^+$ (calcd for $C_{43}H_{54}O_{18}$Na, 881.3208), confirming a molecular formula of the compound GJ-7 as $C_{43}H_{54}O_{18}$; UV(MeOH)$\lambda_{max}$(log ε): 430 (5.33), 454 (5.28), 326 (4.80), 242 (4.78); IR(KBr)$v_{max}$ 972, 1069, 1179, 1227, 1284, 1610, 1697, 2922, 3391 cm$^{-1}$; see Table 3 for $^{13}$C NMR (DMSO-d$_6$, 150 MHz).

Compound GJ-8: red amorphous powder; ESI-MS (positive): m/z 703 [M+Na]$^+$; HR-ESI-MS: m/z 703.2904 [M+Na]$^+$ (calcd for $C_{34}H_{48}O_{14}$Na, 703.2942), confirming a molecular formula of the compound GJ-8 as $C_{34}H_{48}O_{14}$; UV(MeOH)$\lambda_{max}$(log ε): 430 (4.64), 456 (4.59), 322 (3.84), 257 (3.95); IR(KBr)$v_{max}$ 1074, 1229, 1697, 2925, 3400 cm$^{-1}$; see Table 3 for $^{13}$C NMR (DMSO-d$_6$, 150 MHz).

Compound GJ-9: red amorphous powder; ESI-MS (positive): m/z 659 [M+Na]$^+$; HR-ESI-MS: m/z 659.2657 [M+Na]$^+$ (calcd for $C_{32}H_{44}O_{13}$Na, 659.2680), confirming a molecular formula of the compound GJ-9 as $C_{32}H_{44}O_{13}$; UV(MeOH)$\lambda_{max}$(log ε): 438 (4.63), 462 (4.60), 328 (3.90), 261 (3.94); IR(KBr)$v_{max}$ 1071, 1515, 1694, 2921, 3277 cm$^{-1}$; see Table 3 for $^{13}$C NMR (DMSO-d$_6$, 150 MHz).

Compound GJ-10: red amorphous powder; ESI-MS (positive): m/z 645 [M+Na]$^+$; HR-ESI-MS: m/z 645.2519 [M+Na]$^+$ (calcd for $C_{31}H_{42}O_{13}$Na, 645.2523), confirming a molecular formula of the compound GJ-10 as $C_{31}H_{42}O_{13}$; UV(MeOH)$\lambda_{max}$(log ε): 428 (4.56), 453 (4.50), 320 (4.11), 257 (4.10); IR(KBr)$v_{max}$ 1072, 1230, 1700, 2924, 3416 cm$^{-1}$; see Table 3 for $^{13}$C NMR (DMSO-d$_6$, 150 MHz).

TABLE 3

| Pos. | 1 | 2 | 3 | 4 | 5 | 6 | 7 | 8 | 9 | 10 |
|---|---|---|---|---|---|---|---|---|---|---|
| 8 | 166.2 | 166.2 | 166.2 | 166.9 | 169.3 | 166.2 | 166.2 | 166.2 | 166.2 | 166.2 |
| 8' | 167.0 | 167.1 | 166.9 | 166.2 | 166.2 | 166.2 | 169.1 | 167.4 | 194.5 | 169.3 |
| 9 | 125.4 | 125.2 | 125.4 | 126.8 | 128.1 | 125.3 | 125.2 | 125.2 | 125.4 | 125.1 |
| 9' | 126.1 | 127.1 | 125.9 | 125.1 | 125.0 | 125.3 | 127.0 | 126.2 | 136.5 | 127.3 |
| 10 | 140.0 | 139.9 | 140.0 | 139.0 | 137.9 | 139.9 | 139.9 | 139.9 | 139.9 | 139.9 |
| 10' | 139.0 | 138.3 | 139.0 | 140.0 | 140.0 | 139.9 | 138.0 | 138.4 | 149.2 | 137.9 |
| 11 | 124.0$^a$ | 123.8 | 125.2 | 125.2 | 125.5 | 123.9 | 123.8 | 123.8 | 124.1 | 123.7 |
| 11' | 123.9$^a$ | 124.2 | 123.7 | 123.6 | 123.5 | 123.9 | 124.2 | 124.0 | 123.9 | 124.3 |
| 12 | 144.7 | 144.7 | 136.8 | 135.6 | 135.3 | 144.6 | 144.6 | 144.6 | 144.5 | 144.7 |
| 12' | 144.0 | 143.4 | 144.1 | 144.8 | 144.7 | 144.6 | 143.3 | 143.9 | 145.7 | 143.2 |
| 13 | 136.9$^a$ | 137.0 | 135.1 | 135.0 | 135.2 | 136.9 | 136.9 | 136.8$^a$ | 136.8 | 137.0 |
| 13' | 136.8$^a$ | 136.7 | 136.4 | 136.4 | 136.2 | 136.9 | 136.6 | 136.9$^a$ | 137.3 | 136.6 |
| 14 | 136.1 | 136.0 | 134.2 | 134.2 | 133.7 | 136.0$^a$ | 136.0 | 136.0 | 135.9 | 136.0 |
| 14' | 135.7 | 135.3 | 135.9 | 136.0 | 135.9 | 135.9$^a$ | 135.3 | 135.6 | 137.0 | 135.2 |
| 15 | 132.1 | 132.1 | 130.9 | 130.9 | 131.1 | 132.0 | 132.0 | 132.0 | 131.9 | 132.1 |
| 15' | 131.9 | 131.7 | 130.7 | 130.7 | 130.3 | 132.0 | 131.6 | 131.7 | 132.6 | 131.5 |
| 19 | 12.7 | 12.7 | 12.7 | 12.7 | 12.8 | 12.7 | 12.7 | 12.7 | 12.7 | 12.7 |
| 19' | 12.8 | 12.8 | 12.8 | 12.8 | 12.7 | 12.7 | 12.8 | 12.8 | 9.4 | 12.9 |
| 20 | 12.6 | 12.5 | 20.0 | 20.1 | 20.1 | 12.5 | 12.6 | 12.6 | 12.6 | 12.5 |
| 20' | 12.6 | 12.6 | 12.5 | 12.5 | 12.5 | 12.6 | 12.5 | 12.5 | 12.5 | 12.6 |
| 1" | 73.6 | 72.8 | 73.6 | 73.6 |  | 166.7 | 166.7 | 60.1 |  |  |
| 2" | 37.4 | 35.1 | 37.0 | 37.0 |  | 114.8 | 114.8 | 14.2 |  |  |
| 3" | 67.5 | 70.9 | 67.7 | 67.7 |  | 145.5 | 145.5 |  |  |  |
| 4" | 74.2 | 68.5 | 73.4 | 73.4 |  | 124.4 | 124.4 |  |  |  |
| 5" | 66.3 | 70.9 | 66.1 | 66.1 |  | 106.3 | 106.3 |  |  |  |
| 6" | 37.6 | 35.1 | 37.6 | 37.6 |  | 148.0 | 148.0 |  |  |  |
| 7" | 174.8 | 172.1 | 174.7 | 174.7 |  | 138.3 | 138.3 |  |  |  |
| 8" |  |  |  |  |  | 148.0 | 148.0 |  |  |  |
| 9" |  |  |  |  |  | 106.3 | 106.3 |  |  |  |
| 6", 8"-OCH$_3$ |  |  |  |  |  | 56.1 | 56.1 |  |  |  |
| 1''' | 165.6 | 165.7 | 165.5 | 165.5 |  |  |  |  |  |  |
| 2''' | 113.6 | 114.3 | 113.6 | 113.6 |  |  |  |  |  |  |
| 3''' | 145.6 | 145.0 | 145.6 | 145.6 |  |  |  |  |  |  |
| 4''' | 125.2 | 125.6 | 125.4 | 125.4 |  |  |  |  |  |  |
| 5''' | 114.9 | 114.8 | 114.9 | 114.9 |  |  |  |  |  |  |
| 6''' | 145.6 | 145.6 | 145.6 | 145.6 |  |  |  |  |  |  |
| 7''' | 148.5 | 148.4 | 148.5 | 148.5 |  |  |  |  |  |  |
| 8''' | 115.7 | 115.8 | 115.7 | 115.7 |  |  |  |  |  |  |
| 9''' | 121.6 | 121.3 | 121.5 | 121.5 |  |  |  |  |  |  |
|  | 8-Gen | 8-Gen | 8-Gen | 8'-Gen | 8'-Gen | 8-Gen | 8-Gen | 8-Gen | 8-Gen |  |
| 1 | 94.5 | 94.5 | 94.5 | 94.5 | 94.5 | 94.5 | 94.5 | 94.5 | 94.5 | 94.5 |
| 2 | 72.5 | 72.4 | 72.5 | 72.5 | 72.4 | 72.5 | 72.5 | 72.5 | 72.4 | 72.4 |
| 3 | 76.3 | 76.2 | 76.3 | 76.3 | 76.2 | 76.2 | 76.2 | 76.3 | 76.2 | 76.2 |
| 4 | 69.2 | 69.2 | 69.2 | 69.2 | 69.2 | 69.2 | 69.2 | 69.2 | 69.2 | 69.3 |
| 5 | 76.3 | 76.3 | 76.3 | 76.3 | 76.3 | 76.2 | 76.2 | 76.3 | 76.3 | 76.4 |
| 6 | 67.9 | 67.9 | 67.9 | 67.9 | 67.9 | 68.0 | 68.0 | 67.9 | 67.9 | 68.0 |
| 1' | 103.1 | 103.1 | 103.1 | 103.1 | 103.1 | 103.0 | 103.0 | 103.1 | 103.1 | 103.7 |
| 2' | 73.5 | 73.4 | 73.5 | 73.5 | 73.5 | 73.4 | 73.4 | 73.5 | 73.4 | 73.3 |
| 3' | 76.8 | 76.8 | 76.8 | 76.8 | 76.8 | 76.5 | 76.5 | 76.8 | 76.7 | 76.6 |
| 4' | 70.0 | 70.0 | 70.0 | 70.0 | 70.0 | 69.8 | 69.8 | 70.0 | 69.9 | 69.5 |
| 5' | 76.9 | 76.9 | 76.9 | 76.9 | 76.9 | 73.8 | 73.8 | 76.9 | 76.9 | 65.7 |
| 6' | 61.0 | 61.0 | 61.0 | 61.0 | 61.0 | 63.5 | 63.5 | 61.0 | 61.0 |  |
|  |  |  |  |  | 8'-Gen |  |  |  |  |  |
| 1 |  |  |  |  | 94.5 |  |  |  |  |  |
| 2 |  |  |  |  | 72.5 |  |  |  |  |  |
| 3 |  |  |  |  | 76.3 |  |  |  |  |  |
| 4 |  |  |  |  | 69.2 |  |  |  |  |  |
| 5 |  |  |  |  | 76.3 |  |  |  |  |  |
| 6 |  |  |  |  | 67.9 |  |  |  |  |  |
| 1' |  |  |  |  | 103.1 |  |  |  |  |  |
| 2' |  |  |  |  | 73.5 |  |  |  |  |  |
| 3' |  |  |  |  | 76.8 |  |  |  |  |  |
| 4' |  |  |  |  | 70.0 |  |  |  |  |  |
| 5' |  |  |  |  | 76.9 |  |  |  |  |  |
| 6' |  |  |  |  | 61.0 |  |  |  |  |  |

$^a$means signals could be interchangeable with the corresponding position in one compound Example 2: Neuroprotection Effect of Monomers of Crocins of *Gardenia jasminoides* Ellis in SH-SY5Y Cell Damage Models Caused by $H_2O_2$ and L-Glutamic Acid 2.1 Method for Culturing SH-SY5Y Nerve Cells The SH-SY5Y nerve cells were cultured in a DMEM culture medium (containing 5% of fetal calf serum in volume fraction) in an incubator containing 5% $CO_2$ at 37° C., while subculturing every 3 to 4 days. Cells in a logarithmic phase were selected for experiments.

2.2 Method for Screening with Hydrogen Peroxide-Damaged Models

SH-SY5Y cells were inoculated at a concentration of $5 \times 10^3$ in a 96-well plate, and then cultured for 24 h, and 100 µL of a liquid culture medium containing $H_2O_2$ and a crocin-like compound was added to the 96-well plate, such that a final concentration of $H_2O_2$ was 400 µM and a final concentration of the crocin-like compound was 10 µM, 1 µM, 0.1 µM, with each concentration in triplicate, followed by culturing for 24 h. After 24 h, a supernatant was sucked out and discarded, and to each well was added 100 µL of MTT (0.5 mg/mL), followed by incubation for 4 h. A supernatant was sucked out and discarded, to each well was added 150 µL of DMSO, followed by shaking for 10 min, and a wavelength of 570 nm was selected to measure a value of absorbancy on a microplate reader[12]. (Effective rate %=($OD_{crocin-like\ compound}$−$OD_{model}$)/($OD_{control}$−$OD_{model}$)*100). See Table 4 for screening results.

2.3 Method for Screening with L-Glutamic Acid-Damaged Models

SH-SY5Y cells were inoculated at a concentration of $5 \times 10^3$ in a 96-well plate, and then cultured for 24 h, and 100 µL of a liquid culture medium containing L-glutamic acid and a crocin-like compound was added to a 96-well plate, such that a final concentration of L-glutamic acid was 160 mM and a final medication concentration of the crocin-like compound was 10 µM, 1 µM, 0.1 µM, with each concentration in triplicate, followed by culturing for 24 h. After 24 h, a supernatant was sucked out and discarded, to each well was added 100 µL of MTT (0.5 mg/mL), followed by incubation for 4 h. A supernatant was sucked out and discarded, to each well was added 150 µL of DMSO, followed by shaking for 10 min, and a wavelength of 570 nm was selected to measure a value of absorbancy on a microplate reader[13]. (Effective rate %=($OD_{crocin-like\ compound}$−$OD_{model}$)/($OD_{control}$−$OD_{model}$)*100). See Table 5 for results.

TABLE 4

| Sequence No. | Serial No. of Compounds | Cell Model | Concentration of Crocin-like Compound (mol/L) | Survival Rate of Cells with Crocin-like Compound |
|---|---|---|---|---|
| 1 | GJ-1 | $H_2O_2$SY5Y | $10^{-5}$ | 10.39 ± 4.85 |
|  |  | Damage | $10^{-6}$ | 0.17 ± 0.29 |
|  |  | Model | $10^{-7}$ | 0.00 ± 0.00 |
| 2 | GJ-2 | $H_2O_2$SY5Y | $10^{-5}$ | 8.82 ± 6.57 |
|  |  | Damage | $10^{-6}$ | 0.00 ± 0.35 |
|  |  | Model | $10^{-7}$ | 0.00 ± 0.00 |
| 3 | GJ-3/GJ-4 | $H_2O_2$SY5Y | $10^{-5}$ | 5.49 ± 5.57 |
|  |  | Damage | $10^{-6}$ | 0.00 ± 0.00 |
|  |  | Model | $10^{-7}$ | 0.25 ± 0.08 |
| 5 | GJ-6 | $H_2O_2$SY5Y | $10^{-5}$ | 36.38 ± 5.27*** |
|  |  | Damage | $10^{-6}$ | 26.02 ± 3.62** |
|  |  | Model | $10^{-7}$ | 14.56 ± 11.22* |
| 6 | GJ-7 | $H_2O_2$SY5Y | $10^{-5}$ | 18.60 ± 3.43* |
|  |  | Damage | $10^{-6}$ | 6.83 ± 3.63 |
|  |  | Model | $10^{-7}$ | 2.42 ± 4.19 |
| 7 | GJ-8 | $H_2O_2$SY5Y | $10^{-5}$ | 36.60 ± 3.81* |
|  |  | Damage | $10^{-6}$ | 5.09 ± 4.50 |
|  |  | Model | $10^{-7}$ | 2.28 ± 3.95 |
| 8 | GJ-9 | $H_2O_2$SY5Y | $10^{-5}$ | 9.43 ± 1.47 |
|  |  | Damage | $10^{-6}$ | 0.67 ± 1.13 |
|  |  | Model | $10^{-7}$ | 0.00 ± 0.00 |
| 9 | GJ-10 | $H_2O_2$SY5Y | $10^{-5}$ | 33.92 ± 2.30* |
|  |  | Damage | $10^{-6}$ | 16.98 ± 3.74 |
|  |  | Model | $10^{-7}$ | 6.28 ± 5.68 |
| 10 | GJ-11 | $H_2O_2$SY5Y | $10^{-5}$ | 2.20 ± 3.81 |
|  |  | Damage | $10^{-6}$ | 4.29 ± 4.42 |
|  |  | Model | $10^{-7}$ | 2.27 ± 2.82 |
| 11 | GJ-12 | $H_2O_2$SY5Y | $10^{-5}$ | 0.00 ± 0.00 |
|  |  | Damage | $10^{-6}$ | 0.00 ± 0.00 |
|  |  | Model | $10^{-7}$ | 0.00 ± 0.00 |
| 12 | GJ-15 | $H_2O_2$SY5Y | $10^{-5}$ | 0.00 ± 0.00 |
|  |  | Damage | $10^{-6}$ | 0.00 ± 0.00 |
|  |  | Model | $10^{-7}$ | 0.00 ± 0.00 |
| 13 | GJ-16 | $H_2O_2$SY5Y | $10^{-5}$ | 0.00 ± 0.00 |
|  |  | Damage | $10^{-6}$ | 0.00 ± 0.00 |
|  |  | Model | $10^{-7}$ | 0.00 ± 0.00 |

*$P < 0.1$,
**$P < 0.05$,
***$P < 0.01$.

TABLE 5

| Sequence No. | Serial No. of Compounds | Cell Model | Concentration of Crocin-like Compound (mol/L) | Survival Rate of Cells with Crocin-like Compound |
|---|---|---|---|---|
| 1 | GJ-1 | L-Glu SY5Y Damage Model | $10^{-5}$<br>$10^{-6}$<br>$10^{-7}$ | 40.03 ± 3.91**<br>27.63 ± 5.36*<br>9.89 ± 2.93 |
| 2 | GJ-2 | L-Glu SY5Y Damage Model | $10^{-5}$<br>$10^{-6}$<br>$10^{-7}$ | 16.29 ± 14.12<br>7.69 ± 9.01<br>6.68 ± 11.57 |
| 3 | GJ-3/GJ-4 | L-Glu SY5Y Damage Model | $10^{-5}$<br>$10^{-6}$<br>$10^{-7}$ | 12.95 ± 4.01**<br>2.78 ± 3.24<br>1.51 ± 2.62 |
| 5 | GJ-6 | L-Glu SY5Y Damage Model | $10^{-5}$<br>$10^{-6}$<br>$10^{-7}$ | 55.02 ± 0.60<br>48.75 ± 9.49<br>24.51 ± 13.70* |
| 6 | GJ-7 | L-Glu SY5Y Damage Model | $10^{-5}$<br>$10^{-6}$<br>$10^{-7}$ | 74.93 ± 15.36*<br>57.05 ± 10.87<br>42.60 ± 5.40 |
| 7 | GJ-8 | L-Glu SY5Y Damage Model | $10^{-5}$<br>$10^{-6}$<br>$10^{-7}$ | 41.28 ± 7.52*<br>7.39 ± 7.08<br>0.00 ± 0.00 |
| 8 | GJ-9 | L-Glu SY5Y Damage Model | $10^{-5}$<br>$10^{-6}$<br>$10^{-7}$ | 46.12 ± 8.45*<br>38.02 ± 5.15*<br>18.26 ± 5.02 |
| 9 | GJ-10 | L-Glu SY5Y Damage Model | $10^{-5}$<br>$10^{-6}$<br>$10^{-7}$ | 35.20 ± 13.61*<br>33.15 ± 12.55*<br>18.26 ± 5.02 |
| 10 | GJ-11 | L-Glu SY5Y Damage Model | $10^{-5}$<br>$10^{-6}$<br>$10^{-7}$ | 4.80 ± 1.28<br>7.02 ± 4.12<br>9.09 ± 4.62 |
| 11 | GJ-12 | L-Glu SY5Y Damage Model | $10^{-5}$<br>$10^{-6}$<br>$10^{-7}$ | 0.00 ± 0.00<br>0.00 ± 0.00<br>0.00 ± 0.00 |
| 12 | GJ-15 | L-Glu SY5Y Damage Model | $10^{-5}$<br>$10^{-6}$<br>$10^{-7}$ | 0.00 ± 0.00<br>0.00 ± 0.00<br>0.00 ± 0.00 |
| 13 | GJ-16 | L-Glu SY5Y Damage Model | $10^{-5}$<br>$10^{-6}$<br>$10^{-7}$ | 0.00 ± 0.00<br>0.00 ± 0.00<br>0.00 ± 0.00 |
| 14 | GJ-17/GJ-18 | L-Glu SY5Y Damage Model | $10^{-5}$<br>$10^{-6}$<br>$10^{-7}$ | 0.00 ± 0.00<br>0.00 ± 0.00<br>0.00 ± 0.00 |

*$P < 0.1$,
**$P < 0.05$,
***$P < 0.01$.

Experiment results indicate: on the SY5Y cell damage models induced by $H_2O_2$, all of the compounds GJ-1 to GJ-10 manifested good protection effects, with compounds GJ-6, GJ-10, and GJ-8 manifesting more excellent protection effects; on the SY5Y cell damage models induced by L-glutamic acid, all of the compounds GJ-1 to GJ-10 also manifested good protection effects, with compounds GJ-1, GJ-6, GJ-7, GJ-10, GJ-9, and GJ-8 manifesting more excellent protection effects. It also can be obtained from the above experiment results that various compounds had different effectiveness in different damage models, which may be resulted from that a mechanism of $H_2O_2$-induced damage is oxidative stress, while a mechanism of L-glutamic acid-induced damage is excitotoxicity damage caused by an excitatory amino acid, and thus the compounds exert the protective effects against damage through different mechanisms.

What is claimed is:

1. A method for inhibiting or treating Alzheimer's disease in a subject, which comprises administering an effective amount of a crocin-like compound or a pharmaceutically acceptable salt thereof to the subject, wherein the crocin-like compound is selected from

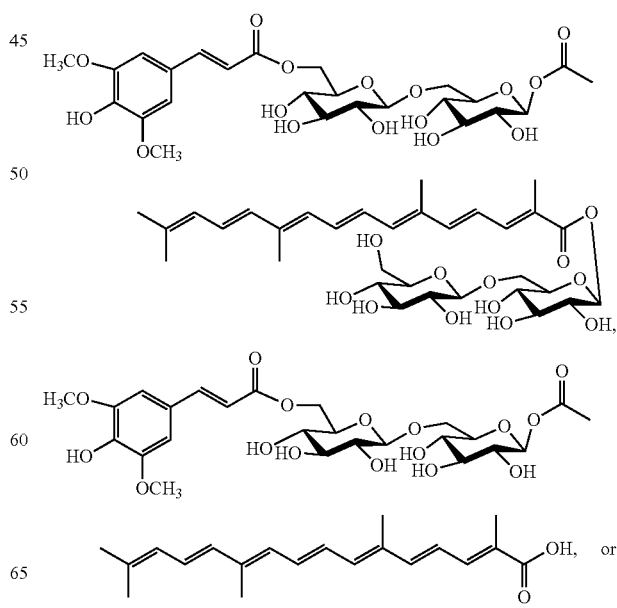

-continued
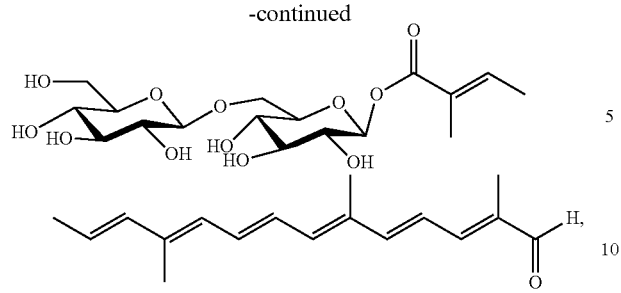
and pharmaceutically acceptable salts thereof.
2. The method according to claim 1, wherein the compound is
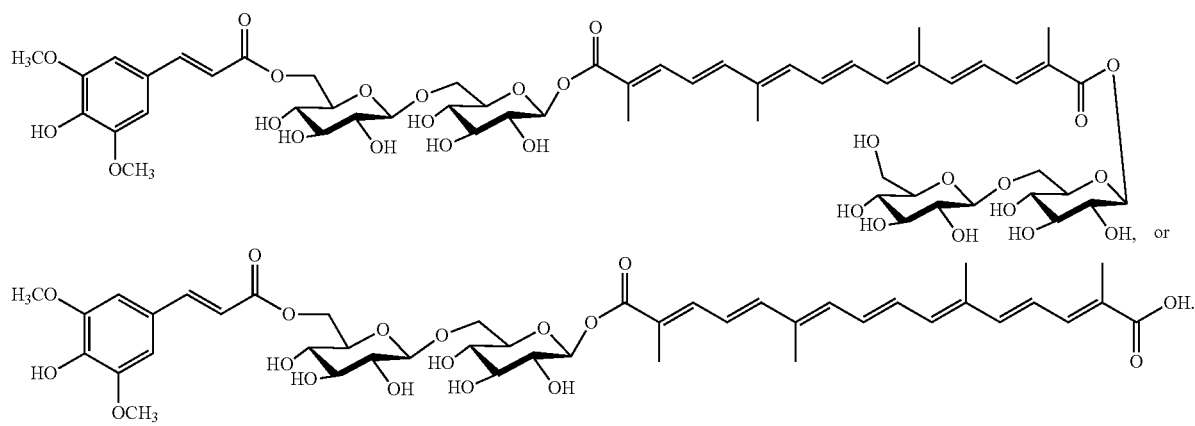
3. The method according to claim 1, wherein the compound is
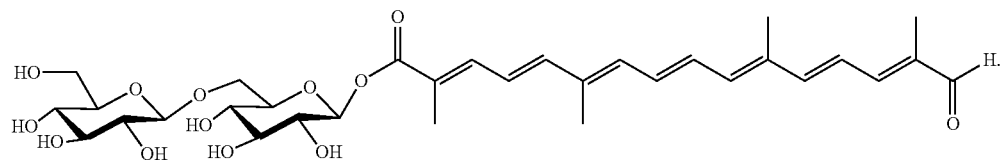
* * * * *